(12) United States Patent
Burton et al.

(10) Patent No.: US 10,549,079 B2
(45) Date of Patent: Feb. 4, 2020

(54) ADHESIVE ASSEMBLIES AND MICRONEEDLE INJECTION APPARATUSES COMPRISING SAME

(71) Applicant: 3M INNOVATIVE PROPERTIES COMPANY, St. Paul, MN (US)

(72) Inventors: Scott A. Burton, Woodbury, MN (US); Chin-Yee Ng, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 235 days.

(21) Appl. No.: 14/652,146

(22) PCT Filed: Dec. 6, 2013

(86) PCT No.: PCT/US2013/073451
§ 371 (c)(1),
(2) Date: Jun. 15, 2015

(87) PCT Pub. No.: WO2014/099404
PCT Pub. Date: Jun. 26, 2014

(65) Prior Publication Data
US 2015/0320990 A1    Nov. 12, 2015

Related U.S. Application Data

(60) Provisional application No. 61/740,941, filed on Dec. 21, 2012.

(51) Int. Cl.
*A61M 37/00*    (2006.01)
(52) U.S. Cl.
CPC .... *A61M 37/0015* (2013.01); *A61M 2037/003* (2013.01); *A61M 2037/0023* (2013.01); *A61M 2209/088* (2013.01)

(58) Field of Classification Search
CPC .............. A61M 37/0015–2037/0061; A61M 2005/14252; A61M 2005/14284;
(Continued)

(56) References Cited

U.S. PATENT DOCUMENTS

RE24,906 E    12/1960 Ulrich
3,389,827 A   6/1968 Abere
(Continued)

FOREIGN PATENT DOCUMENTS

AU    2012-211391    8/2012
EP    0902696        3/1999
(Continued)

OTHER PUBLICATIONS

International Search Report for PCT International Application No. PCT/US2013/073451 dated Mar. 4, 2014, 5 pages.

*Primary Examiner* — Amber R Stiles
*Assistant Examiner* — Laura C Schell

(57) ABSTRACT

Adhesive assemblies and microneedle injection apparatuses comprising same. The apparatus (100) can include a housing (102) having a base and an opening (115) formed in the base; and an applicator comprising a microneedle array (104), the microneedle array comprising a first major surface (111) and microneedles (105). The applicator can be movable between a first position, and a second position in which at least a portion of the microneedle array extends through the opening in the base. The apparatus can further include an adhesive assembly (118), which can be adhered to the base of the housing. The adhesive assembly can include an extension (125) that extends at least partially into the area defined by the opening, such that when the applicator is in the second position, at least a portion of the first major surface of the microneedle array is in contact with the extension of the adhesive assembly.

16 Claims, 12 Drawing Sheets

(58) Field of Classification Search
CPC .. A61M 2005/1585; A61M 2005/1586; A61M 2209/088
See application file for complete search history.

(56) References Cited

U.S. PATENT DOCUMENTS

| | | | |
|---|---|---|---|
| 4,112,213 | A | 9/1978 | Waldman |
| 4,310,509 | A | 1/1982 | Berglund |
| 4,323,557 | A | 4/1982 | Rosso |
| 4,595,001 | A | 6/1986 | Potter |
| 4,737,410 | A | 4/1988 | Kantner |
| 6,689,100 | B2 | 2/2004 | Connelly |
| 7,250,037 | B2 | 7/2007 | Shermer |
| 2004/0138612 | A1* | 7/2004 | Shermer ............... A61M 5/142 604/93.01 |
| 2005/0228340 | A1* | 10/2005 | Cleary ................ A61B 17/205 604/46 |
| 2005/0283114 | A1* | 12/2005 | Bresina ................ A61M 5/158 604/93.01 |
| 2008/0233348 | A1 | 9/2008 | Ishiwatari |
| 2010/0222743 | A1* | 9/2010 | Frederickson ....... A61B 17/205 604/136 |
| 2011/0172637 | A1* | 7/2011 | Moga ................ A61M 5/14248 604/506 |
| 2011/0213335 | A1 | 9/2011 | Burton |
| 2012/0109066 | A1 | 5/2012 | Chase |
| 2012/0123387 | A1 | 5/2012 | Gonzalez |
| 2012/0136310 | A1 | 5/2012 | Kadamus |
| 2012/0143136 | A1 | 6/2012 | Constantineau |
| 2012/0302844 | A1 | 11/2012 | Schnidrig |

FOREIGN PATENT DOCUMENTS

| | | |
|---|---|---|
| WO | WO 2002-30300 | 4/2002 |
| WO | WO 2005-072794 | 8/2005 |
| WO | WO 2006-108185 | 10/2006 |
| WO | WO 2010-056541 | 5/2010 |
| WO | WO 2010-056543 | 5/2010 |

* cited by examiner

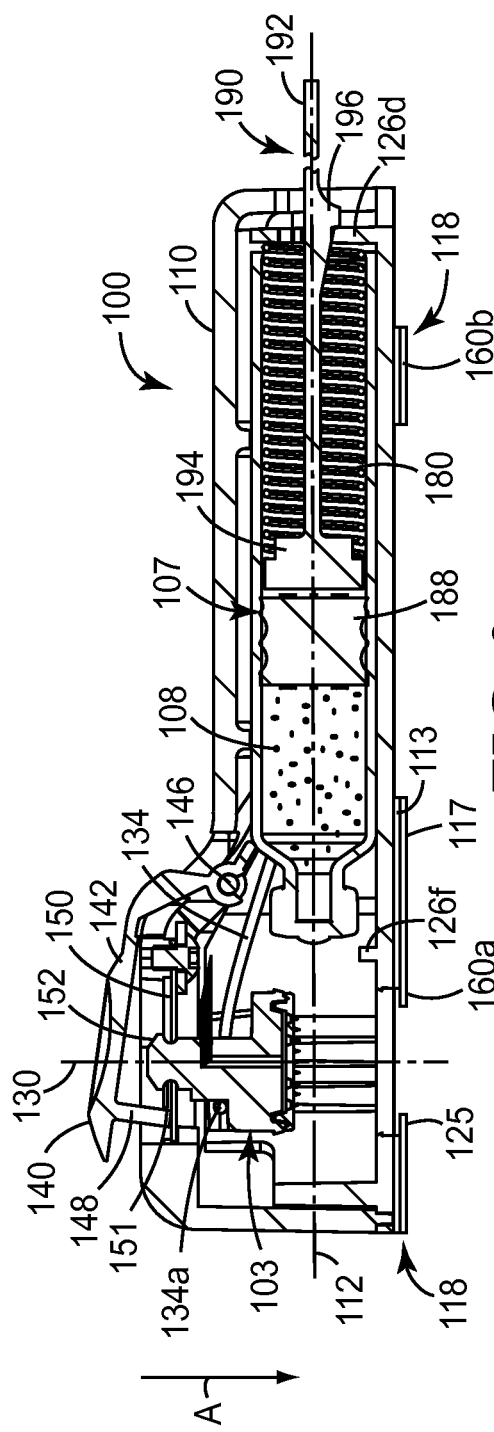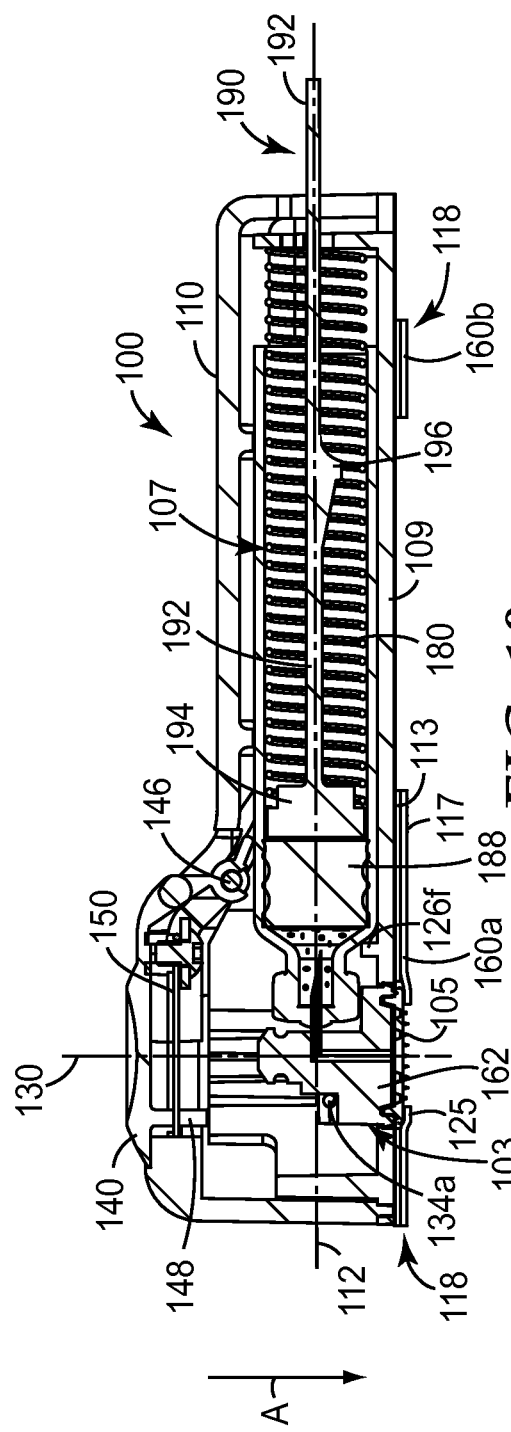

ADHESIVE ASSEMBLIES AND MICRONEEDLE INJECTION APPARATUSES COMPRISING SAME

CROSS REFERENCE TO RELATED APPLICATIONS

This is a national stage filing under 35 U.S.C. § 371 of PCT/US2013/073451, filed Dec. 6, 2013, which claims priority to U.S. Provisional Application No. 61/740,941, filed Dec. 21, 2012, the disclosure of which is incorporated herein by reference in its entirety.

FIELD

The present disclosure generally relates to adhesive assemblies, or systems, comprising one or more layers, and microneedle injection apparatuses comprising such adhesive assemblies.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle arrays can be used in conjunction with an applicator device capable of being used several times or as a single-use device. The microneedle arrays are generally used once and then discarded.

SUMMARY

The present inventors recognized that issues related to applying microneedles include the ability to effectively and consistently insert the needles to a desired depth in the skin, the ability to reliably hold the microneedles in proper contact with the skin during the period of administration, and the ability to apply consistent force for delivery.

The present disclosure generally relates to an adhesion assembly, or system, for use with a transdermal microneedle injection apparatus that is used to treat skin, deliver an active agent to the skin and/or withdraw fluid from the skin. The adhesive assemblies of the present disclosure provide improved skin adhesion of the microneedle injection apparatus, which can hold the microneedles in proper contact with the skin (and to a desired depth) and minimize leakage of fluid onto the skin surface during fluid delivery and/or withdrawal.

Some aspects of the present disclosure provide a microneedle injection apparatus. The apparatus can include a housing having a base and an opening formed in the base, the opening defining an area. The apparatus can further include an applicator comprising a microneedle array, the microneedle array comprising a first major surface and a plurality of microneedles that protrude from the first major surface. The applicator can be movable between (i) a first position in which the microneedle array is recessed within the housing such that the microneedle array does not extend beyond the base of the housing, and (ii) a second position in which at least a portion of the microneedle array extends through the opening in the base and beyond the base of the housing. The apparatus can further include an adhesive assembly adhered to the base of the housing, the adhesive assembly including an extension that extends at least partially into the area defined by the opening, such that when the applicator is in the second position, at least a portion of the first major surface of the microneedle array is in contact with the extension of the adhesive assembly.

The phrase "injection apparatus" refers to an integrated device capable of delivering or extracting a fluid over a certain period and is not limited to devices intended solely for an infusion. Accordingly, an injection apparatus may be used, for example, for injecting fluid into the dermis or extracting fluid from tissue.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The phrase "hollow microneedle" refers to a specific microscopic structure that is designed for piercing the stratum corneum to facilitate the delivery of drugs through the skin. By way of example, microneedles can include needle or needle-like structures, as well as other structures capable of piercing the stratum corneum and delivering liquid drug formulations to skin or tissue layers beneath the stratum corneum.

In discussing the applicators of the present disclosure, the term "downward," and variations thereof, is sometimes used to describe the direction in which microneedles are pressed into skin, and "upward" to describe the opposite direction. However, those of skill in the art will understand that the applicators can be used where the microneedles are pressed into skin at an angle to the direction of the earth's gravity, or even in a direction contrary to that of the earth's gravity, and these terms are only used for simplicity and clarity to describe relative directions.

Other features and aspects of the present disclosure will become apparent by consideration of the detailed description and accompanying drawings.

BRIEF DESCRIPTION OF THE DRAWINGS

FIG. 9 is a longitudinal cross-sectional view of the microneedle injection apparatus of FIGS. 1-8, shown in a primed but inoperative condition.

FIG. 10 is a longitudinal cross-sectional view of the microneedle injection apparatus of FIGS. 1-9, shown in an operative condition.

DETAILED DESCRIPTION

Figure 1:
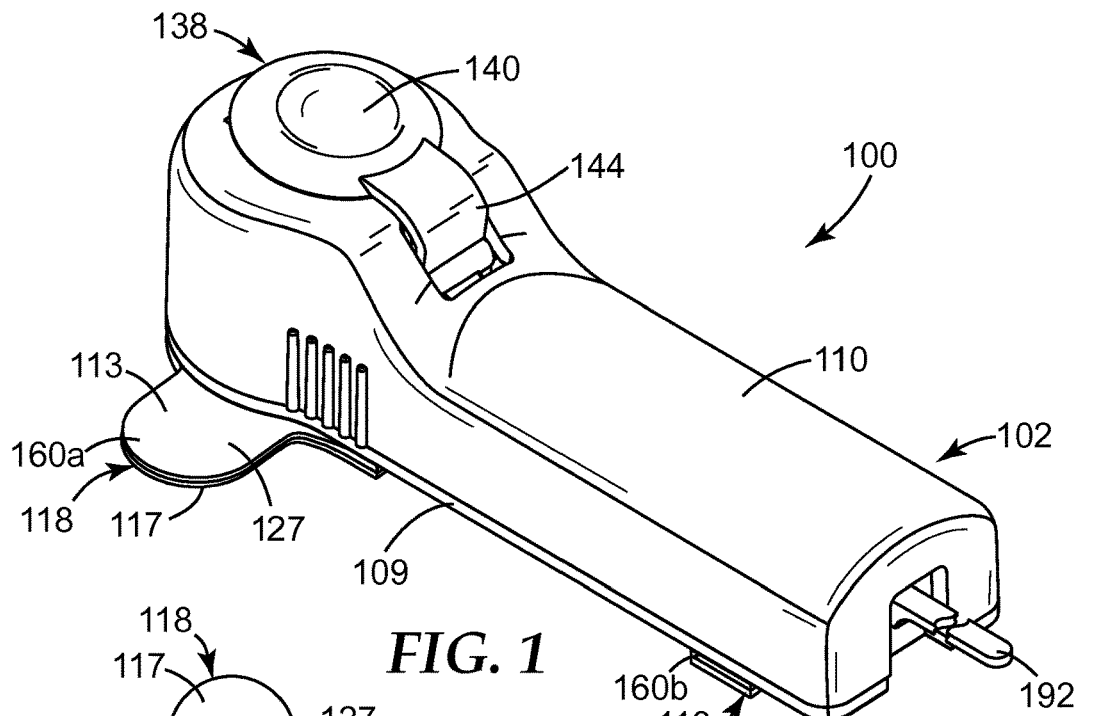
FIG. 1 is a perspective view of a microneedle injection apparatus according to one embodiment of the present disclosure, the microneedle injection apparatus comprising an adhesive assembly according to one embodiment of the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to an adhesion assembly, or system, for use with a transdermal (e.g., intradermal) microneedle injector, or injection apparatus, comprising an array of microneedles that is applied to skin (or a biological membrane) to treat the skin (i.e., create small holes or perforations or micropores in the skin) and/or to deliver an active agent to the skin (or withdraw fluid from the skin). The adhesive assemblies of the present disclosure provide improved skin adhesion of the microneedle injection apparatus to the skin by relieving forces that tend to fracture a top skin layer under an adhesive of the injection apparatus during microneedle insertion. The adhesive assemblies of the present disclosure can also hold the microneedles in the dermis during high pressure fluid delivery preventing leakage of medicinal fluid onto the skin surface.

The adhesion assemblies of the present invention can provide an adhesive (e.g., annular in shape) that surrounds the microneedle array and one or more adhesive extensions (or "fingers") that extend in toward the microneedle array from the adhesive annulus, which can help adhere the microneedle array to the skin. The adhesive extension(s) can have pressure sensitive adhesive on both sides. When the array is actuated, the array can strike and adhere to the adhesive extension(s) and push the adhesive extension(s) against the skin, thus promoting adhesion of the array to the skin. The extension can include one or more slots (or slits or vents or notches, etc.) that can be oriented outwardly (e.g., radially) from the center of the microneedle array, thereby separating the extension into a plurality of extensions and allowing air to escape during microneedle insertion. The adhesive assemblies of the present disclosure can further include a compliant (e.g., shock absorbing) layer that can improve skin adhesion during microneedle insertion and during a wear or treatment period, e.g., by maximizing the adhesive peel angle as the skin bends or contorts.

As used herein, the term "annular" or derivations thereof can refer to a structure having an outer edge and an inner edge, such that the inner edge defines an opening. For example, an annular cover can have a circular or round shape (e.g., a circular ring) or any other suitable shape, including, but not limited to, triangular, rectangular, square, trapezoidal, polygonal, etc., or combinations thereof. Furthermore, an "annulus" of the present disclosure need not necessarily be symmetrical, but rather can be an asymmetrical or irregular shape; however, certain advantages may be possible with symmetrical and/or circular shapes.

Without wishing to be bound by theory, the following generally describes potential issues with some existing microneedle injection apparatus and theories for how the adhesive assemblies of the present disclosure can solve or at least partially overcome these issues.

Microneedle injection apparatuses are generally used to transfer fluid from an injector reservoir to a site within a body. Injector leakage can be defined as the fluid that is intended to be injected to a body site, but is not administered to the desired injection site. Microneedle injection apparatus, and especially intradermal injectors, are generally designed to deliver fluid to the intradermal space. During use of such microneedle injectors, leakage is often found on the surface of the skin. After the injector is adhered to the skin, the device can be actuated (releasing an insertion spring), which can urge a microneedle array downward, causing the microneedles to insert into the skin. A fluid reservoir, or cartridge, can then be released, causing a septum on the cartridge to be pierced (forming a fluidic pathway from the fluid reservoir to the dermis) and also pressurizing the fluid in the cartridge. When the fluid is pressurized, fluid may leak onto the skin surface via the skin-microneedle interface.

In order to insert microneedles into the skin, due to the elastic, deformable nature of the skin, and to avoid skin tenting, the microneedles are generally inserted into the skin at high speeds, for example, between 5 and 14 m/s. During microneedle insertion, the microneedle array base is urged downward (e.g., by an insertion spring, as described in greater detail below). In the downward state, the microneedle array base (e.g., a "first major surface" of the microneedle array) protrudes past the injector base, e.g., by at least about 1.2 mm. The protrusion of the first major surface of the microneedle array past the injector base can help hold the skin against the microneedles during fluid injection.

In some existing microneedle injection apparatuses, the adhesive used to couple the injector base to the skin includes an annular adhesive surrounding an opening in the base through which the microneedles applicator protrude when actuated. When the microneedles make high-speed contact with the skin, a radial shockwave is generally produced, which can fracture the skin, or a topmost layer thereof (i.e., stratum corneum) under the adhesive in a random manner. During insertion, 30 to 70 percent of the stratum corneum can be fractured under the adhesive depending on the insertion speed, the dome height of the skin, the proximity of the adhesive to the array, and the array protrusion distance beyond the injector base.

The stratum corneum is the outermost layer of the epidermis, consisting of dead cells (corneocytes). Corneocytes are formed in the basal layer of the epidermis, and it takes about 14 days to move this layer to the skin surface where it flakes off (called desquamation). Corneodesmosomes (modified desmosomes) facilitate cellular adhesion by linking adjacent cells within this epidermal layer. These complexes are degraded by proteases, eventually permitting cells to be shed at the surface.

The corneodesmosomes near the surface of the skin are the weakest, allowing the stratum corneum to flake off, revealing fresh stratum corneum beneath. When pressure sensitive adhesive is placed on the skin, it adheres to the surface corneocytes, which also have the weakest corneodesmosomes. When the microneedle array impacts the skin during insertion, a radial shock wave can tear apart the top layers of the stratum corneum that are in contact with the adhesive surrounding the opening in the applicator base.

At high insertion speeds (e.g., about 8 m/s), a pressure sensitive adhesive can act like a solid. As a result, when a peel force is exerted on the adhesive-skin interface at high speeds, the adhesive generally does not debond from the skin. Rather, the corneocytes stay adhered to the adhesive and the stratum corneum fractures or tears apart. Once torn apart, the corneodesmosomes do not reattach even if they are brought together in close proximity; and adhesion is lost. Leakage at the microneedle-skin interface can occur due to the fact that microneedles are inserted into the skin to a depth of only about 500 microns. During fluid delivery at high pressure (~140 kilopascals (kPa), or 20 psi), the fluid can exit the needle approximately 300 microns under the skin surface. The fluid pressure in the dermis can push the skin away from the microneedle. If the adhesion is poor near the microneedle, the skin can push away from the microneedle and fluid can leak onto the skin surface. This potential problem can be exacerbated when multiple microneedles are used.

One way to solve this stratum corneum fracturing problem is to provide an adhesive assembly of the present disclosure that can strike the skin at the same instant and with the same velocity as the microneedles.

The present inventors have discovered that some existing microneedle injectors leaked at low insertion speeds because the microneedles did not insert deeply enough into the skin. However, at higher insertion speeds, injection success (i.e., lack of leakage) was also diminished by what can be referred to as a "trampoline effect," a "billiard ball effect" and decreasing skin adhesion. The trampoline effect can occur when the microneedles stretch the skin during needle insertion. When the microneedle injector (e.g., a base thereof) is pressed against the skin, the skin under the microneedle array can dome up into the cavity and provide a trampoline-like membrane that the microneedle array interacts with during insertion. During insertion, some of the kinetic energy of the microneedles can be temporarily transferred to the skin; and when the array slows to a certain point the skin returns some of the energy to the microneedle array, similar to a person jumping on a trampoline. The billiard ball effect can occur when the microneedle array reaches its end of travel and strikes the injector base (e.g., from the inside of the injector). After the microneedles insert into the skin, the insertion spring continues to urge the array downward until it reaches the injector base at which time at least a portion of the microneedle applicator (e.g., a base thereof and/or a first major surface of the array) makes contact with the injector base. At high insertion speeds, the microneedle applicator can make contact with and bounce off of the injector base, forcing the injector base downward and the array upward. The skin, however has downward momentum, and may slide off of the microneedles as this occurs (i.e., a "skin inertia" effect). In addition, at high insertion speeds, the microneedle array can strike the skin with such a high force that it tears the skin away from the adhesive adhering the injector base to the skin.

Adhesive assemblies, or systems, of the present disclosure, and microneedle injection apparatuses comprising such adhesive assemblies, can improve skin adhesion and can inhibit skin fracturing and tearing during microneedle insertion during (and/or after) microneedle insertion and can thus improve transdermal (e.g., intradermal) injection success, e.g., by at least one of (i) slowly decelerating the microneedles during skin insertion; (ii) allowing air to vent out from between the microneedle array and the skin during microneedle insertion; (iii) providing good adhesion when the microneedle array protrusion distance is greater than zero; (iv) maximizing the depth of microneedle penetration in the skin; (v) minimizing the trampoline effect; (vi) minimizing the billiard ball effect; (vii) minimizing the skin inertia effect; and (viii) minimizing peeling off of the injector from skin during the wear period by maximizing the adhesive peel angle when the skin bends.

Particularly, the adhesive assemblies of the present disclosure can accomplish one or more of the following: (1) counteract stratum corneum fracturing and tearing, (2) adhere the microneedle array to the skin, and (3) promote adhesion of the injector base to the skin at a periphery of the microneedle array by changing the peel angle in response to skin movement.

The apparatus of the present description includes embodiments that may be activated by a single actuation to automatically and reliably penetrate a patient's skin by a microneedle array, for instance a hollow microneedle array, and then automatically release and dispense thereto a stored fluid from a reservoir (e.g., a ready-to-use drug cartridge) in a controlled manner that ensures consistent uptake. Advantageously, customizable and efficacious delivery of a wide variety of fluids and dosages to individual patients may be achieved in a relatively trauma free manner, while at the same time minimizing leakage of fluid around the apparatus onto a skin surface instead of effectively delivering the fluid into the skin.

FIGS. 1-13C illustrate a microneedle injection apparatus (which can also be referred to as a "controlled fluid release apparatus") 100 according to one embodiment of the present disclosure. The microneedle injection apparatus 100 comprises a housing 102; a microneedle applicator (or just "applicator" for simplicity) 103 comprising a microneedle array 104 comprising a base or first major surface 111 from which one or more hollow microneedles 105 protrude downwardly; and a fluid storage and delivery system 106 including reservoir 107 (which, in some embodiments, may be a drug cartridge). As described below, in some embodiments, the microneedle array 104 can include a microneedle applicator plate 163, and in some embodiments, the first major surface 111 can be at least partially defined or provided by the microneedle applicator plate 163.

In some embodiments, the microneedle injection apparatus 100 can enable the reservoir 107 to be installed by manufacturers, assemblers, or users. In addition, the microneedle injection apparatus 100 can enable the reservoir 107 and the hollow microneedles 105 to be replaced, thereby permitting reuse. In addition, the reservoirs may be more easily cleaned, sterilized, filled, and refilled as compared to microneedle devices having fixed or dedicated drug reservoirs integral therewith.

The microneedle injection apparatus 100 is adaptable to be "worn" by a patient during infusion/injection of fluid 108 (see, e.g., FIGS. 9, 10 & 13A-13C). In these exemplary embodiments, the microneedle injection apparatus 100 may be directly applied to a patient's skin (see, e.g., FIG. 12) to accommodate ambulatory movement while keeping hollow microneedles 105 at an appropriate penetration depth(s).

Any substance that can be formulated in a fluid and delivered via hypodermic injection may be used, including any pharmaceutical, nutraceutical, cosmeceutical, diagnostic, and therapeutic agents (collectively referred to herein as "drug" for convenience). Examples of drugs that may be useful with the present invention include but are not limited to ACTH (e.g., corticotropin injection), luteinizing hormone-releasing hormone (e.g., Gonadorelin Hydrochloride), growth hormone-releasing hormone (e.g., Sermorelin Acetate), cholecystokinin (Sincalide), parathyroid hormone and fragments thereof (e.g., Teriparatide Acetate), thyroid releasing hormone and analogs thereof (e.g., protirelin), secretin and the like, Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as Hirulog, IgE suppressors, Insulin, insulinotropin and analogs, Insulin-like growth factors, Interferons, Interleukins, Luteinizing hormone, Luteinizing hormone releasing hormone and analogs, Heparins, Low molecular weight heparins and other natural, modified, or synthetic glycoaminoglycans, M-CSF, metoclopramide, Midazolam, Monoclonal antibodies, Peglyated antibodies, Pegylated proteins or any proteins modified with hydrophilic or hydrophobic polymers or additional functional groups, Fusion proteins, Single chain antibody fragments or the same with any combination of attached proteins, macromolecules, or additional functional groups thereof, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne Japanese encephalitis, pneumococcus, streptococcus, typhoid, influenza, hepatitis, including hepatitis A, B, C and E, otitis media, rabies, polio, HIV, parainfluenza, rotavirus, Epstein Barr Virsu, CMV, chlamydia, non-typeable haemophilus, *Moraxella catarrhalis*, human papilloma virus, tuberculosis including BCG, gonorrhoea, asthma, atherosclerosis malaria, *E-coli*, Alzheimer's Disease, *H. Pylori*, salmonella, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, and sexual hypofunction and tranquilizers. The present description envisions that even a gaseous fluid may be utilized.

Figure 2:
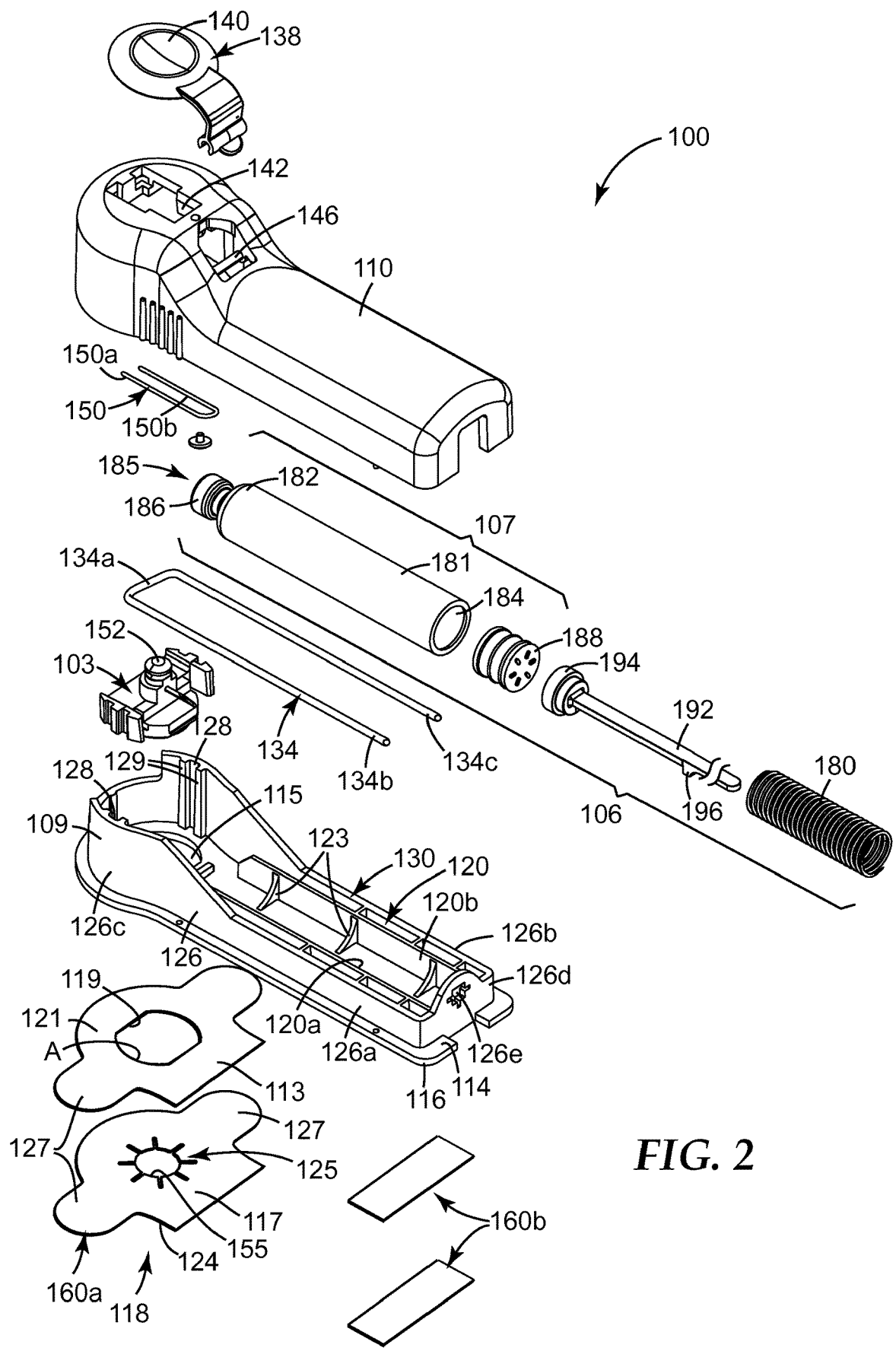
FIG. 2 is an exploded perspective view of the apparatus of FIG. 1, showing that the microneedle injection apparatus further includes a microneedle applicator according to one embodiment of the present disclosure.

The housing 102 may be self-contained and compactly constructed to provide a relatively low profile and small footprint for, among other factors, ease of use and patient comfort. As shown in FIGS. 1 and 2, the housing 102 may include lower housing portion 109 and mating upper housing portion 110 that provides a cover. Lower and upper housing portions 109 and 110 may be coupled together using a variety of coupling means, including, but not limited to, one or more of magnets, hook-and-loop fasteners, adhesives (or adhesive tapes, labels, or the like), cohesives, heat sealing, welding (e.g., sonic (e.g., ultrasonic) welding), any thermal bonding technique (e.g., heat and/or pressure applied to one or both of the components to be coupled), other suitable coupling means, or combinations thereof. For example, lower and upper housing portions 109 and 110 may be connected together by a hinge (not shown) that allows pivoting of clamshell-like lower and upper housing portions 109 and 110. The housing 102 may be made of suitable lightweight materials compatible for delivering fluids of the kind noted above. The materials of housing 102 may include, but are not limited to, plastics, metals, composite materials, and combinations thereof. The lower housing portion 109 may include a base 114 (see FIG. 2), which may be generally planar, defining opening 115 in the base 114 for allowing hollow microneedles 105 to be displaced by first stored energy device 134. The base 114 defines a relatively large and generally planar surface, first major surface 116 (FIG. 2). In some embodiments, the base 114 is sufficient to support the microneedle injection apparatus 100 in a comfortable manner when worn.

An adhesive assembly 118 may be joined to all or part(s) of the first major surface 116 of the base 114. The adhesive assembly 118 (see, e.g., FIG. 2) can be covered by a release liner or layer (not shown) prior to use, and the release layer can be removed prior to application of the apparatus 100 to the patient. Example of suitable release liners are described below. The adhesive assembly 118 is illustrated as being generally coextensive to the first major surface 116 of the base 114. The present illustrated embodiment also contemplates that adhesive assembly 118 may be located immediately adjacent the opening 115 in the base 114. As shown, the adhesive assembly 118 can include one or more optional release tabs 127 that can facilitate removal of the adhesive assembly 118 from a skin surface when the treatment or wear period has expired.

The release tabs 127 can be formed of different materials than the rest of the adhesive assembly 118 and can be formed in a separate process from the rest of the adhesive assembly 118 and/or by different methods. That is, even in embodiments employing the release tabs 127, the release tabs 127 need not include all of the same layers as the rest of the adhesive assembly 118. For example, in some embodiments in which the first layer 113 and the second layer 117 are both employed in the adhesive assembly 118, the release tabs 127 may only include one layer which or may not be provided by (or the same as) one of the first layer 113 or the second layer 117. In addition, because the release tabs 127 are primarily employed to facilitate removal of the apparatus 100, the release tabs 127 (if employed) need not include any adhesive. However, in some embodiments, the release tabs 127 may include adhesive. In some embodiments, no release tabs 127 are employed, in some embodiments, one release tab 127 is employed, in some embodiments, two release tabs 127 (as shown by way of example only) are employed, and so on.

Many suitable pressure sensitive adhesives may be used in the adhesive assembly 118, such as, but not limited to, one or more of polyacrylates, polyisobutylenes, polysiloxanes, or combinations thereof.

As shown in FIG. 2, the adhesive assembly 118 can include one or more separate sections 160 or portions arranged along the base 114 of the housing 102 and positioned to be adhered to the first major surface 116 of the base 114. Two separate sections 160 are illustrated by way of example only as including a main or head portion 160*a* configured to be located adjacent a head of the microneedle injection apparatus 100 comprising the microneedle applicator 103, and a second portion 160*b* configured to be located under the portion of the microneedle injection apparatus 100 comprising the reservoir 107. However, it should be understood that, in some embodiments, the adhesive assembly 118 can include only the main portion 160*a*, or the adhesive assembly 118 can include a plurality of second sections 160*b* located along the length of the base 114. Alternatively, in some embodiments, the adhesive assembly 118 can include one continuous piece that extends along at least a portion of the base 114. The main portion 160*a* will be described in greater detail with respect to FIGS. 3A-3C.

Figure 3:
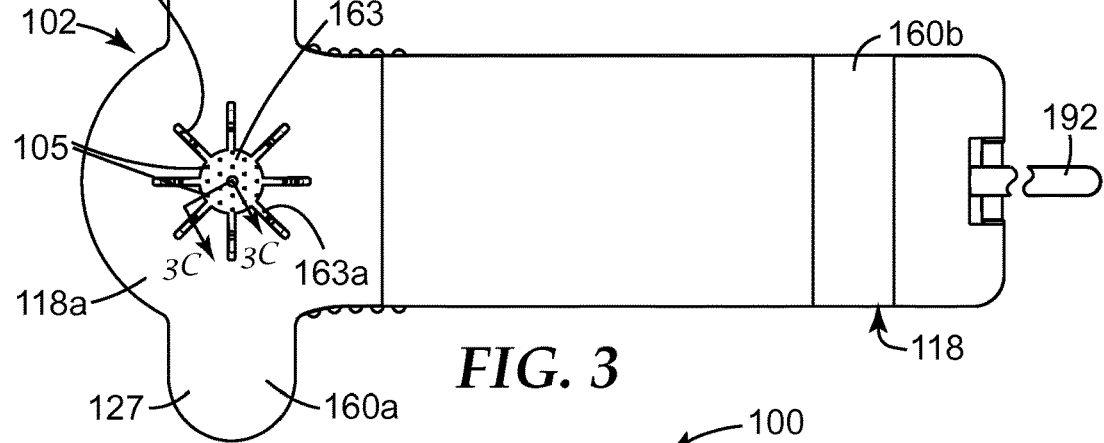
FIG. 3 is a bottom plan view of the apparatus of FIGS. 1 and 2.
Figure 4:
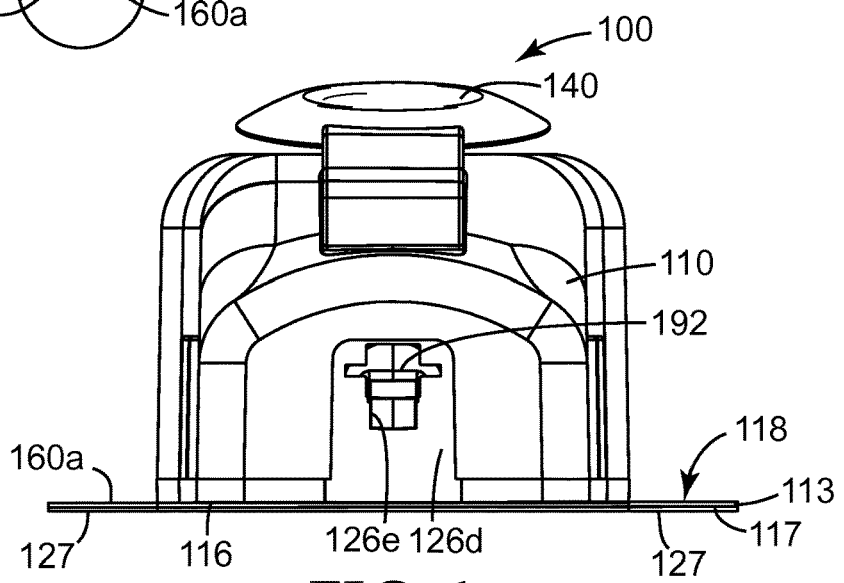
FIG. 4 is an end elevational view of the apparatus of FIGS. 1-3, in a primed condition.
Figure 3A:
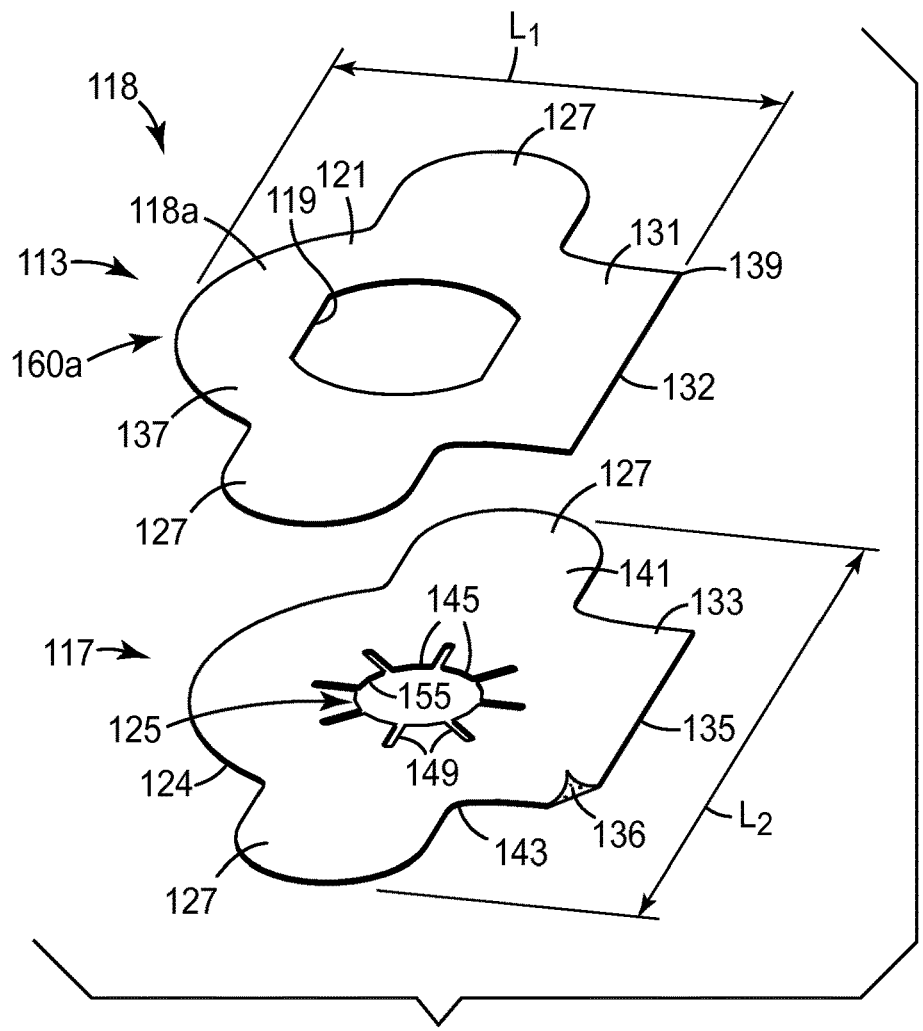
FIG. 3A is an exploded perspective view of the adhesive assembly of FIGS. 1-3, the adhesive assembly comprising an adhesive layer.
Figure 3B:
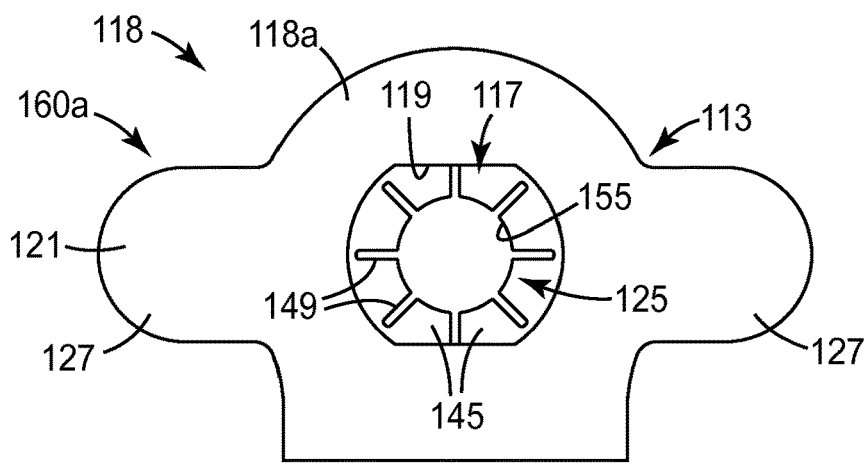
FIG. 3B is a top plan view of the adhesive assembly of FIGS. 1-3 and 3A.
Figure 3C:
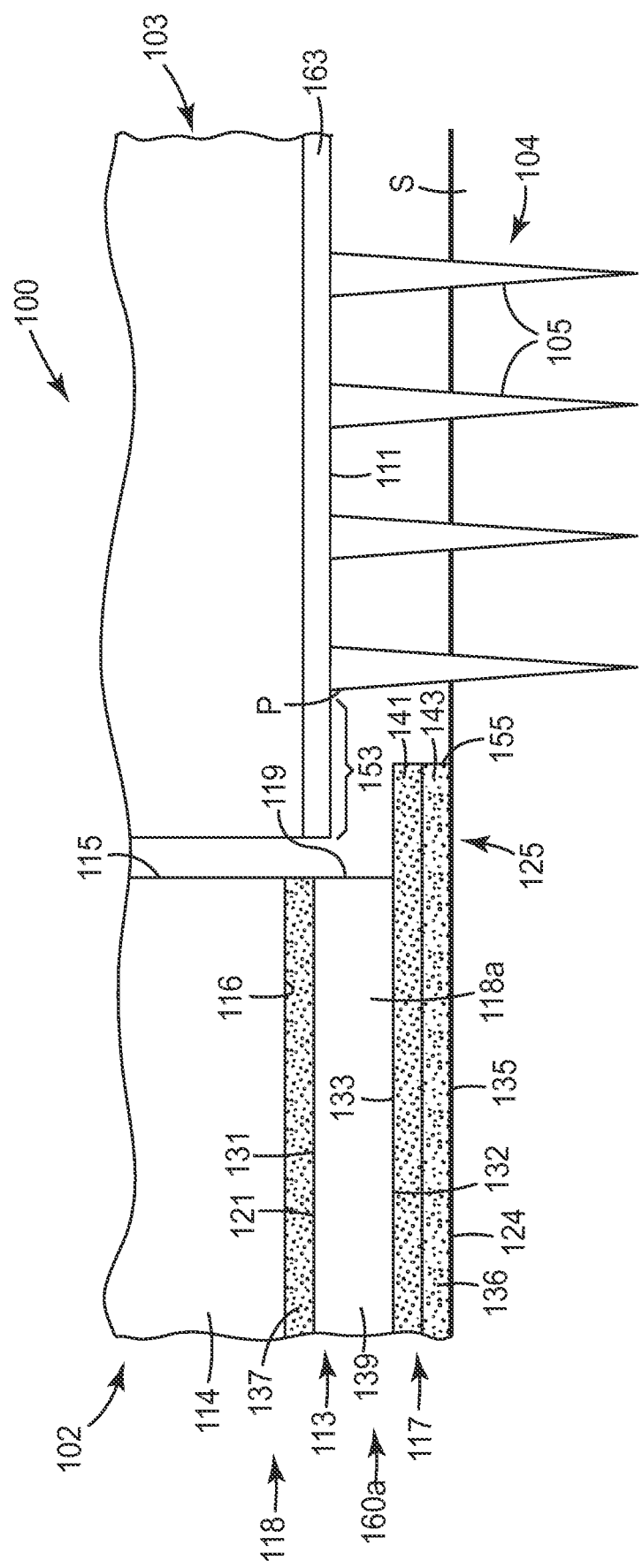
FIG. 3C is a schematic cross-sectional view of the microneedle injection apparatus of FIGS. 1-3 and 3A-3B, taken along line 3C-3C of FIG. 3.
Figure 5:
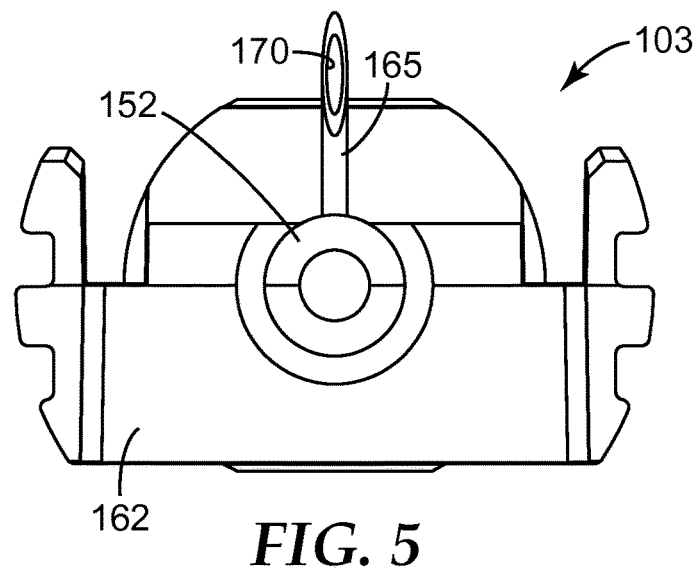
FIG. 5 is a top plan view of the microneedle applicator of FIG. 2.

The adhesive assembly 118 can include an overall first (or top or non-tissue-facing) side 121 positioned toward the base 114 of the housing 102 configured to be coupled (e.g., adhered) to the base 114 (e.g., the first major surface 116 of the base 114) of the housing 102; and an overall second (or bottom or tissue-facing) side 124 opposite the first side 121, which is configured to be adhered to a skin surface (see, e.g., skin or skin surface S in FIG. 3C).

The adhesive assembly 118 further includes at least one extension 125 that extends at least partially into an area A (see FIGS. 2 and 3A) that is generally defined by the opening 115 in lower housing portion 109 and in the base 114 of the housing 102, such that when the microneedle array 104 is moved to protrude beyond the base 114 (and, particularly, beyond the first major surface 116 of the base 114, e.g., to penetrate the skin S), the first major surface 111 of the microneedle array 104 that is located adjacent the microneedles 105 (i.e., the non-structured, non-featured surface around and between the microneedles 105) contacts the extension 125 of the adhesive assembly 118.

In some embodiments, the extension 125 can include adhesive on at least the second side 124 of the adhesive assembly 118 to adhere to the skin S, and in some embodiments, the extension 125 can include adhesive on the first side 133 of the second layer 117 (which can be the first side 121 of the overall adhesive assembly 118 in embodiments in which the first layer 113 is not employed) and the second side 124 (e.g., provided by the second side 133 of the second layer 117), such that the extension 125 is configured to adhere to both the first major surface 111 of the microneedle array 104 and skin S when the applicator 103 has been moved into its treatment and/or delivery position (i.e., when the microneedle array 104 has been inserted into the skin S).

As further shown in FIGS. 2 and 3A-3C, in some embodiments, the adhesive assembly 118 can be formed of more than one layer (i.e., at least two layers). By way of example only, as shown, in some embodiments, the adhesive assembly 118 can include a first (or top, or support, or shock absorbing) layer 113 and a second (or bottom, or adhesive) layer 117. The first layer 113 has a first side 131 configured to be coupled to the base 114 and a second side 132 opposite the first side 131 and configured to be coupled to the second layer 117. The first side 131 of the first layer 113 can form the overall first side 121 of the adhesive assembly 118. The second layer 117 has a first side 133 configured to be coupled to the second side 132 of the first layer 113, and a second side 135 opposite the first side 133 and configured to be coupled to the skin S. The second side 135 of the second layer 117 can form the overall second side 124 of the adhesive assembly 118. As shown, in some embodiments, the first layer 113 and the second layer 117 of the adhesive assembly 118 can both form or include a portion of the release tabs 127.

As shown, the first layer 113 can include an annular portion 118a that surrounds an opening 119 that aligns with the opening 115 in the base 114 of the housing 102, such that the aperture 119 can be in registry with the opening 115 of the housing 102. As a result, the area A can be defined by one or both of the opening 115 and the opening 119. The second layer 117 can include the extension 125 that extends into the area A, and the second side 124 of the second layer 117 can include a skin-contact adhesive 136.

Adhesives present in the annular portion 118a may have higher strength adhesive qualities than other portions or sections of the adhesive assembly 118 to ensure an even more secure coupling to the skin in the area surrounding needle penetration. It will be appreciated that variations may be made to the formulations of adhesive layer 118 for varying the strength of the adhesive securing the microneedle injection apparatus to a patient's skin as well as other bodily tissues.

The first layer 113 is an optional layer and can function as a support or shock absorbing layer in the adhesive assembly 118. Thus, by way of example, the first layer 113 is illustrated as including a shock absorbing (or support) layer 139. As shown in FIG. 3C, the shock absorbing layer 139 can be adhered to the base 114 with a securing adhesive 137. That is, the first side 131 of the first layer 113 can include the securing adhesive 137. However, it should be understood the shock absorbing layer 139 can be coupled to the base 114 (e.g., the first major surface 116 thereof) using a variety of coupling means, including, but not limited to, one or more of magnets, hook-and-loop fasteners, adhesives, cohesives, heat sealing, welding (e.g., sonic (e.g., ultrasonic) welding), any thermal bonding technique (e.g., heat and/or pressure applied to one or both of the components to be coupled), other suitable coupling means, or combinations thereof. In embodiments employing the securing adhesive 137, the first layer 113 can be provided with a release liner (not shown) covering the securing adhesive 137 on its first side 131.

As shown, in embodiments employing the first layer 113, the extension 125 can be free of the shock absorbing layer 139. That is, the shock absorbing layer 139 can align with the opening 115 and not extend into the area A defined by the opening 115. The second layer 117 can include one or more adhesive layers. As shown by way of example only, the second layer 117 is illustrated as including two adhesive layers—a first (or top or non-tissue-facing) adhesive layer 141 comprising adhesives similar to the securing adhesive 137 for coupling to the first layer 113 (and particularly, for coupling to the shock absorbing layer 139); and a second (or bottom or tissue-facing) adhesive layer 143 comprising the skin-contact adhesive 136. In some embodiments, as shown, the extension 125 can be formed from both the first adhesive layer 141 and the second adhesive layer 143. In such embodiments, the first adhesive layer 141 is further configured to adhere to the first major surface 111 of the microneedle array 104 in the area of the extension 125. However, in some embodiments, the first side 133 of the second layer 117 in the area or region of the extension 125 can be non-adhesive, such that the first adhesive layer 141 does not extend into or form a portion of the extension 125. The second layer 117 which can consist only of one or more adhesive layers, can be provided with a release liner (not shown) on its first side 133 and its second side 135. Examples of suitable securing adhesives (i.e., for the securing adhesive 137 and the first adhesive layer 141) and skin-contact adhesives (i.e., for the skin-contact adhesive 136) are described in greater detail below.

In embodiments employing more than one section of adhesive assembly 118 along the length of the base 114, the plurality of sections can each include both the first layer 113 and the second layer 117, or each of the sections can include only the second layer 117, or a portion thereof, even in embodiments in which the main portion (i.e., the portion shown in greater detail in FIGS. 3A-3C) adjacent a head of the microneedle injection apparatus 100 is formed of at least two layers.

In some embodiments, the extension 125 can be continuous about a periphery of the opening 119 or about the opening 115 in the base 114. However, in some embodiments, as shown, the extension 125 can be discontinuous and can include a plurality of sections (or fingers) 145 that are each separated from an adjacent section by a vent (or slot, or slit, or notch, or recess) 149. In some embodiments, air can get compressed between the first major surface 111 of the microneedle array 104 and the skin S during insertion and/or impact, which can inhibit proper microneedle insertion and proper adhesion of the first major surface 111 to the extension 125 of the adhesive assembly 118. The vents 149 can be positioned to allow compressed air to escape during insertion and/or impact to minimize such effects.

In embodiments employing a plurality of sections or fingers 145 in the extension, the sections 145 can each extend from a location adjacent a periphery of the opening 115 (or the opening 119) at least partially into the area A defined by the opening 115. In some embodiments, the vents 149 can be wholly contained within the area A (as shown), or the vents 149 can extend from a location within the area A past an edge of the opening 115 (or the opening 119). By way of example only, the sections 145 are shown as extending inwardly (e.g., radially inwardly) from the periphery of the opening 115 (and the opening 119), and the vents 149 are shown as extending outwardly (e.g., radially outwardly) from a position toward a center of the microneedle array 104 toward the outer periphery of the opening 115 (and the opening 119).

As further shown, in some embodiments, the extension 125 can extend only partially into the area A, such that the extension 125 does not extend past an outer periphery P (see FIG. 3C) of the microneedle array 104 of microneedles 105. Rather, in such embodiments, the extension 125 can extend into the area A, adjacent the first major surface 111 of the microneedle array 104, only to a location adjacent the outer periphery (or perimeter) P. This outer region or area of the first major surface 111 of the microneedle array 104 can sometimes be referred to as a sidewalk and is referenced by numeral 153 in FIG. 3C. As a result, in some embodiments, the extension 125 can be in the form of an annulus (or be annular) and can further define an opening 155 therein that is sized to accommodate the microneedle array 104.

The shape of the opening 119 (and the opening 115) is shown by way of example only as having a barrel shape or a "racetrack" shape with two rounded opposing ends and two flat opposing sides. However, the shape and configuration of the adhesive assembly 118 as a whole, as well as the shape and configuration of the opening 119, can be tailored to accommodate any microneedle injection apparatus and any microneedle applicator 103.

The shape of the extension 125 is shown by way of example only, however, this shape can allow the second layer 117 of the adhesive assembly 118 outside of the area A to adhere to the base 114 (e.g., via the optional first layer 113), while leaving the extension 125 (e.g., in the form of the sections 145) free to adhere to the moving microneedle applicator 103. When the injector is placed on the skin S, the skin S adheres to the second side 124 of the adhesive assembly 118 (e.g., the second side 135 of the second layer 117 of the adhesive assembly 118), including in the area of the extension 125. When the microneedles 105 insert into the skin S, the microneedle array sidewalk 153 can strike (and optionally adhere to) the first side 133 of the extension 125. The force of the insertion can (a) push the extension 125 toward the skin S promoting skin adhesion; and (b) can push the microneedle array sidewalk 153 toward the extension 125, thereby promoting microneedle array adhesion to the skin S. Due to the extensibility of the shock absorbing layer 139, as well as the optional adhesive layers (i.e., layers 137, 141 and 143), the microneedle applicator 103 can make a "soft landing" that modulates the impact force on the skin surface and minimize the trampoline and billiard ball effects described above.

As described above, when the microneedle applicator 103 impacts the skin, the force can generate a radial shock wave around the applicator 103, which can cause the applicator 103 to bounce off of the skin (sometimes referred to as "bounce back"). The shock absorbing layer 139, if employed, can dampen the force of the shock wave that is generated by the impact of the applicator 103 on the skin. The shock absorbing layer 139 can be compressible and extensible in the z-axis (i.e., in a direction normal to the plane of the first major surface 111 of the microneedle array 104 and the first major surface 116 of the base 114). The shock absorbing layer 139 can adhere to the adhesive second layer 117 (e.g., via the first adhesive layer 141 of the second layer 117), however, the second layer 117 may partially debond from the shock absorbing layer 139 during microneedle array insertion (depending on the array protrusion distance). The shock absorbing layer 139 can also bend and change the peel angle of the second layer 117, which can increase the peel force and thereby prevent the second layer 117 from peeling away from the skin during (or just after) microneedle insertion. The shock absorbing layer 139 (depending on its compressibility) can regulate the array protrusion distance during microneedle insertion. The shock absorbing layer 139 can act to help the second layer 117 conform to a curved skin surface and promote skin adhesion.

The shock absorbing layer 139 can be formed of a variety of materials, including, but not limited to, a non-woven material, a woven material, an open cell foam, a closed cell foam, a dampening elastomer, other suitable energy dissipative elements that would absorb and dissipate the resulting recoil and vibration following impact of the microneedles 105, or a combination thereof. By way of example only, in some embodiments, the shock absorbing layer 139 can be formed of a non-woven fabric available under the trade designation SONTARA® from DuPont Corporation, Wilmington, Del. (e.g., SONTARA® 8005). In some embodiments, the shock absorbing material exhibits elasticity (i.e., can stretch easily), e.g., at the velocities experienced by the applicator 103. In some embodiments, the shock absorbing layer 139 can include multiple layers of shock absorbing material (or said another way, in some embodiments, the adhesive assembly 118 (or the first layer 113) can include multiple shock absorbing layers 139), and such layers can be formed of the same or different materials.

The remainder of the microneedle injection apparatus 100 and its operation will now be described in greater detail.

Continued reference is made to FIG. 2 wherein there is illustrated a retaining wall assembly 120 which is upstanding from the base 114 and is spaced laterally from the edges thereof. The retaining wall assembly 120 may include a pair of generally upstanding and spaced apart retaining wall portions 120a and 120b having curved ribs 123 for retaining and guiding reservoir 107 along longitudinal axis 107a (see FIG. 12). Retaining wall portions 120a and 120b are disposed inwardly of laterally disposed and upstanding external wall 126 that includes lateral wall portions 126a and 126b generally parallel to retaining wall portions 120a and 120b. External wall 126 may include rounded portion 126c and rear wall portion 126d. Integrally molded to rounded portion 126c may be a pair of diametrically opposed inwardly facing channel portions 128 defined by respective ribs 129 facing inwardly. External wall 126 may include rear wall portion 126d having wall opening 126e.

The channel portions 128 retain and guide the microneedle applicator 103 for displacement along a path generally perpendicular to the first major surface 116, indicated by arrow A in FIGS. 9 and 10. Vertical axis 130 is generally normal to that of the longitudinal axis 107a. While in one exemplary embodiment, the motion of the microneedle applicator 103 may be at substantially 90 degrees with respect to first major surface 116, it will be appreciated that the generally normal path may deviate from 90 degrees to assume orientations that can penetrate deep enough to deliver an intended dosage. Such paths generally ensure positive penetration to a targeted intradermal depth. As such, consistent uptake and efficacious administering of the fluids are enhanced.

Microneedle injection apparatus 100, illustrated for example in FIGS. 2 and 9, depicts first stored energy device 135 that is actuatable for applying force to the microneedle applicator 103 in a direction generally normal to the first major surface 116. In some embodiments, such actuated force allows for movement of the applicator 103 in a controlled manner, thereby ensuring application of the necessary forces for hollow microneedles 105 to penetrate the skin of a subject.

Some existing injection apparatuses may suffer from the shortcoming that users pushing down on microneedle dispensing devices (not shown) may use too much force or too little force, thereby resulting in unwanted variations in penetration force and depth. In some aspects, the microneedle injection apparatuses of the present disclosure overcome this shortcoming of other devices.

In one embodiment, the first stored energy device 134 may be a leaf-like spring arranged to apply to the applicator 103 a controlled force, ensuring a consistent penetration to a targeted depth range. In the exemplary embodiment, as illustrated in, for example, FIG. 2, the first stored energy device 134 may be comprised of a generally U-shaped leaf-like spring. A curved portion 134a of the first stored energy device 134 is configured to rest on, or may otherwise be coupled or supported directly on, the applicator 103.

As illustrated in FIG. 2, the first stored energy device 134 may include leg portions 134b, 134c that are configured to be disposed between spaced apart retaining wall portions 120a and 120b and lateral wall portions 126a and 126b. Advantageously, such positioning of the first stored energy device 134 within the housing 102 immediately adjacent the reservoir 107 not only simplifies the construction and assembly of microneedle injection apparatus 100, but also makes for a smaller footprint and lower profile, thereby significantly improving the overall construction.

In one exemplary embodiment, for example, the first stored energy device 134 may be 7.5 cm×0.0625" (0.159 cm) outside diameter stainless steel spring with a gap distance of about 12 mm. The present disclosure contemplates a variety of similar springs and spring constructions that may be used.

The present inventors recognized a tendency for the microneedle applicators to recoil following impact against the skin due to factors that include the springiness of the first stored energy device 134 and the elasticity of skin. It is also generally advantageous that hollow microneedles 105 penetrate to a predetermined depth in the dermis and remain at that depth (or within a certain depth range) during infusion. Some embodiments of the present description have the effect of dampening this recoil, thereby providing more precise delivery of the microneedle arrays described herein.

In one exemplary embodiment, the first stored energy device 134 is not fixed to the applicator 103. As such, following impact, the first stored energy device 134 may freely recoil upwardly and vibrate without partially or totally withdrawing or lifting hollow microneedles 105 from the skin and their intended penetration depths. As such, the potential for leakage of the fluid to the surface of the skin occurring may be reduced, minimized or even eliminated. Alternatively, the first stored energy device 134 may be made to maintain a positive pressure on the applicator 103 throughout the skin impact and penetration, thereby avoiding potential partial or even total withdrawal of the microneedles 105.

It will be appreciated that the magnitude and frequency of spring recoil and vibration is directly related to primary factors such as the spring's free length, mass and material properties, and any tension or preload. Other factors may include the spring's shape and configuration, such as a multi-element stacked leaf-like spring, as in a stacked flat leaf spring arrangement; single straight length as in a single piece of round spring tempered wire; shaped wire-formed U-shaped, etc. Furthermore, the first stored energy device 134 may be made with any cross-section, including, but not limited to, round, square, rectangular, any regular polygon, irregular in shape or even varying along its length. Such shape profiles may thereby confer stiffness and rigidity at portions where needed.

The first stored energy device materials may include a carbon steel (e.g., music wire), oil tempered based alloys (e.g., beryllium copper, phosphor bronze), or other suitable alloys (e.g., Elgiloy™ cobalt alloy commercially available from Elgin Specialty Metals, Elgin, Ill., USA). While in the present exemplary embodiment, a metallic spring may be used that has a relatively high spring energy constant for sake of compactness, it is also possible that a less compact, non-metallic (e.g., plastic) spring element may be utilized, such as where the spring element is primed and fired within a short time frame.

The first stored energy device 134 is actuatable for applying force to the applicator 103 carrying hollow microneedles 105, typically at a velocity before impact ranging from between about 2 and about 20 m/s before applicator 103 impacts a patient's skin. More typically, the hollow microneedles 105 can strike a patient's skin at a velocity before impact ranging from between about 4 and about 12 m/s, and in some embodiments, at a velocity ranging from between about 8 and about 9.5 m/s.

Reference is made now to FIGS. 1, 2, 4, and 8. The upper housing portion 110 may have a construction, such as illustrated, to envelop and cooperate with the lower housing portion 109 as noted. The upper housing portion 110 may be made of a single-piece, shell-like construction that is sized and shaped to generally match the lower housing portion 109 for mating therewith. In the illustrated exemplary embodiment, the upper housing portion 110 may also be made of a plastic, such as polycarbonate, acrylic and other similar materials. The upper housing portion 110 may also be transparent to allow a user to visually inspect the extent of the infusion. Alternatively, the upper housing portion 110 may have a window (not shown) that similarly allows a user to easily visually observe the extent of the fluid being dispensed as well as piston displacement as will be described. This is particularly advantageous in situations involving infusions occurring over relatively long periods of time.

Figure 8:
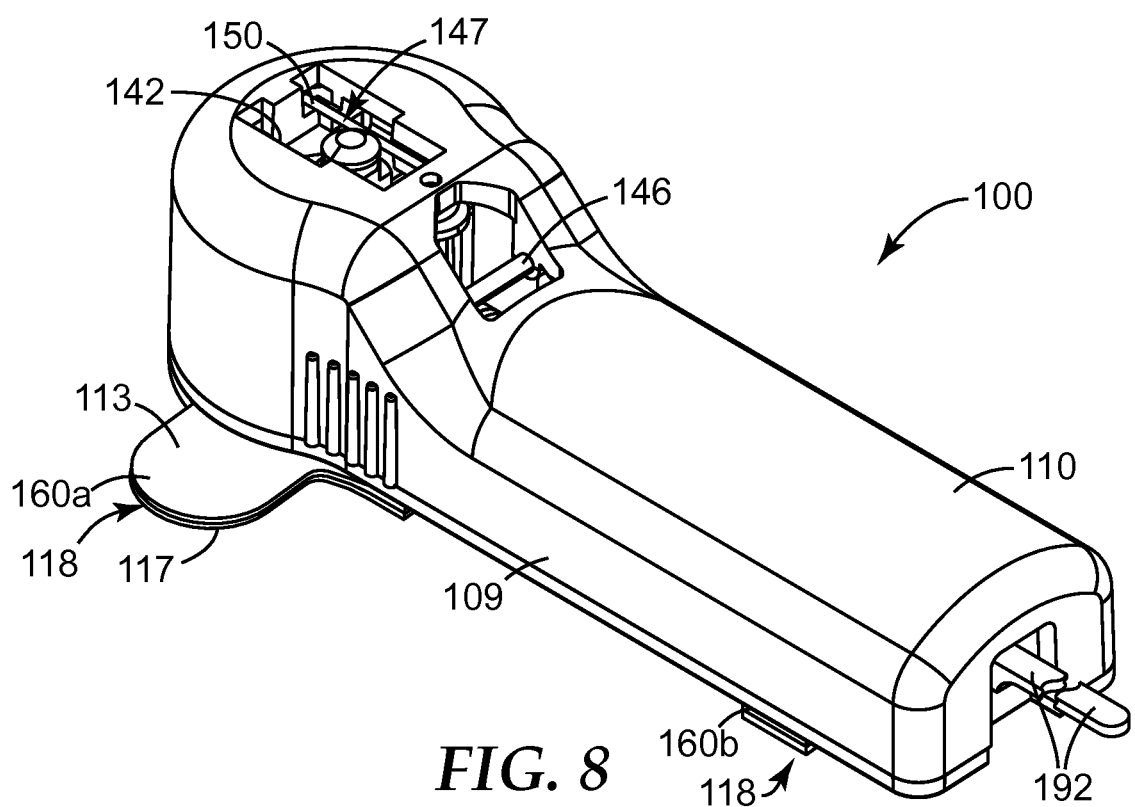
FIG. 8 is a perspective view of the microneedle injection apparatus of FIGS. 1-7, similar to FIG. 1, with an actuator removed.
Figure 11:
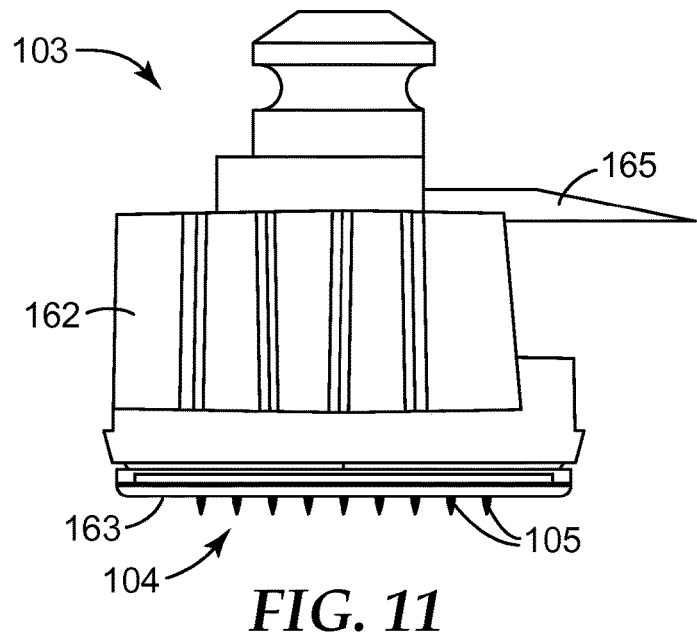
FIG. 11 is a side elevational view of the microneedle applicator of FIGS. 5-7.

The housing 102 also includes an actuator 138 (see FIGS. 1, 2 & 8). The actuator 138 has a finger engageable portion 140 that is adapted to cover actuator opening 142 (e.g., FIGS. 2, 8-10) formed in the upper housing portion 110. A tab portion 144 extends from the finger engageable portion 140 and is hingedly connected to pivot about hinge pin 146 (see FIGS. 8-10) located in the upper housing portion 110. This allows the actuator 138 to pivot from a position corresponding to a first (or primed, or unactuated, or non-treatment) position $P_1$ of the microneedle applicator 103 (see FIG. 9), to a position that corresponds to a second (actuated or treatment) position $P_2$ of the applicator 103 where the hollow microneedles 105 are in their penetrating position, as illustrated in FIGS. 10, 12, 13B and 13C. In the first position $P_1$, the microneedle array 104 is recessed within the housing 102, such that the microneedle array 104 does not extend beyond the base 114 (and particularly, the first major surface 116 of the base 114) of the housing 102. In the second position $P_2$, at least a portion of the microneedle array 104 extends through the opening 115 in the base 114 and beyond the base 114 (e.g., beyond the first major surface 116 of the base 114) of the housing 102, e.g., to penetrate skin when the microneedle injection apparatus 100 is coupled to a patient's skin.

With continued reference to FIGS. 8-10, the present description includes releasable retaining mechanism 147 for releasing first stored energy device 134 from its first primed position $P_1$. In the present illustrated exemplary embodiment, releasable retaining mechanism 147 may include plunger 148 depending from finger engageable portion 140. Plunger 148 is sized, shaped, and arranged to release applicator 103 when moved downwardly as by pressing down on finger engageable portion 140. During downward movement, plunger 148 engages resilient engaging device 150, such as a single piece catch spring. Resilient engaging device 150 may have a generally U-shape (see FIG. 2) and may be fixed to the interior of the upper housing portion 110, as by a fastener, so as to be immediately below actuator opening 142. Resilient engaging device 150 may include a pair of generally spaced apart and parallel resilient leg portions 150a and 150b that are adapted to be engaged and spread apart by the plunger 148 when the latter is pressed downwardly therebetween. Resilient leg portions 150a and 150b are engageable with peripheral groove 151 (see FIGS. 7 and 9) on the upper retaining member 152 of the applicator 103 to form an interlocking relationship that maintains the latter in the first position $P_1$.

To release the applicator 103, the finger engageable portion 140 is depressed downwardly, as viewed in the drawings, such as when a user commences an infusion/injection process. As a result, the plunger 148 spreads resilient leg portions 150a and 150b apart sufficiently to release them from the peripheral groove 151 (see FIGS. 7 and 9) of the upper retaining member 152. This frees first stored energy device 134 to drive or force the applicator 103 downwardly, generally along the vertical axis 130, so that applicator 103 can be moved (e.g., released) to the second position $P_2$ (see FIGS. 10 and 12). The resilient leg portions 150a and 150b that are stressed when in peripheral groove 151 may return to an unstressed condition after the applicator 103 has been forced downwardly by the first stored energy device 134.

The present description envisions that the applicator 103 may be primed before being shipped from a manufacturer or assembler of the microneedle injection apparatus, but also allows a user to prime the apparatus in a manner to be described. When the applicator 103 is to be primed, as may be described in more detail hereinafter, it will be forced (e.g., pulled or pushed) upwardly until upper retaining member 152 spreads leg portions 150a and 150b apart, whereby the latter resiliently snap into the peripheral groove 151, thereby retaining the applicator 103 in its first position $P_1$. The present description envisions other kinds of releasable retaining mechanisms that may be used for releasably retaining the applicator 103 in the first position $P_1$ prior to release. Such mechanisms include, but are not limited to, a wide variety of spring-biased holding members, such as latches, snap-fits, annular snap-fits, and other similar devices. It will be understood that the applicator 103 need not be stored or shipped in its primed condition (i.e., in the first position $P_1$), but may be shipped in a non-primed condition.

Reference is now made to FIGS. 5-7, 9, 10, 12, and 13A-13C for illustrating the applicator 103 in the second position $P_2$ that may be useful, for instance, as a skin penetrating position for distributing or dispensing fluid 108 from a ready-to-use reservoir 107 to a patient. As noted, the reservoir 107 may be more easily cleaned, sterilized, filled, and refilled as compared to microneedle devices having fixed or dedicated drug reservoirs integral therewith For carrying out the penetration, the applicator 103 may include the microneedle array 104 on the bottom or penetrating side of manifold carrier 162. In one exemplary embodiment, the microneedle array 104 may be permanently attached or removably attached to the applicator 103. In another exemplary embodiment, the microneedle array 104 may include microneedle applicator plate 163. Formed in microneedle applicator plate 163 is an array of hollow microneedles 105 protruding therefrom.

In one exemplary embodiment, the hollow microneedles 105 typically may have a length of greater than 100 µm to about 3 mm. In other embodiments, the hollow microneedles 105 may have a length that ranges from about 250 µm to about 1500 mm, more typically, a length of from 500 µm to 1000 µm. In some embodiments, the hollow microneedles 105 may penetrate into the skin of a patient to a depth of from about 150 µm to 1500 µm. More typically, they penetrate into the skin to a depth of from about 50 µm to 400 µm, more typically from about 100 µm to 300 µm. It will be appreciated that the depth of penetration of the hollow microneedles 105 may not be the full length of the hollow microneedles themselves.

The hollow microneedles 105 may typically have a spacing of about no less than 0.7 mm on average between adjacent hollow microneedles. More typically, microneedle array 104 may have the hollow microneedles 105 spaced an average of at least 2 mm apart from each other. Hollow microneedles 105 may have an average channel bore (not shown) of 10 to 500 µm$^2$ cross-sectional area, more typically, the average channel bore may range from 80 to 300 µm$^2$. In some embodiments, the hollow microneedles 105 may have a spacing density of 3 to 18 microneedles per cm$^2$. The bores (not shown) may allow a fluid to be dispensed from the microneedle array 104 as a whole at a rate of about 20 µL/min to 500 µL/min, e.g., as disclosed in U.S. Patent Publication No. 2011/0213335 (Burton et al.), which is incorporated by reference herein. In some embodiments, rates of up to 1000 µL/min, with a backpressure during delivery of up to 400 kPa (58 psi) can be achieved. The bore may terminate in an exit hole or port (not shown) located on a sidewall of each hollow microneedle, or a sidewall portion that is adjacent the needle tip.

The present description contemplates all forms of microneedles that can deliver fluid through them. Also, it will be understood that the foregoing values are illustrative and not necessarily limiting. It will be further understood that the present description envisions the use of other needle assemblies for injection and infusion besides hollow microneedles. As such, the needle lengths may be longer than noted above. Also, the depth of penetration of hollow microneedles 105 may vary from needle to needle, so the above values can be considered "average" values over the entire array 104. Hollow microneedles typically enable penetration into the dermis of a patient in a manner that minimizes or reduces trauma. It will be understood that a relationship of trauma and various infusion/injection parameters exist.

Reference is now made to, for example, FIGS. 12, and 13A-13C for illustrating a piercing needle 165, which may comprise at least one cannula, manifold inlet tube, or other form of piercing needle. The piercing needle 165 is provided as an inlet on the manifold carrier 162. The piercing needle 165 establishes a fluid path that fluidly connects the fluid 108 in reservoir 107 to a carrier reservoir 166 (see FIG. 12) above the microneedle array 104 by way of a fluid pathway 168, such as illustrated. One or more piercing needles 165 are envisioned. As such, the fluid 108 may be dispensed by infusion/injection into a patient's skin (signified by "S" in FIG. 12) through the hollow microneedles 105. In one exemplary embodiment, the piercing needle 165 may comprise a lumen 170 (e.g., FIGS. 5 & 12) formed and extending therethrough. The lumen 170 is connected fluidically to the fluid pathway 168. The piercing needle 165 is dimensioned in length to ensure opening a sealed but openable end of the reservoir 107, as will be explained below. The piercing needle 165 also has sufficient strength to accomplish this without buckling or otherwise failing. A wide variety of materials may be used for the piercing needle 165. Towards this end, the materials may include, but are not limited to, metals including stainless steel, plastics, ceramics, composite materials, and combinations thereof.

Figure 12:
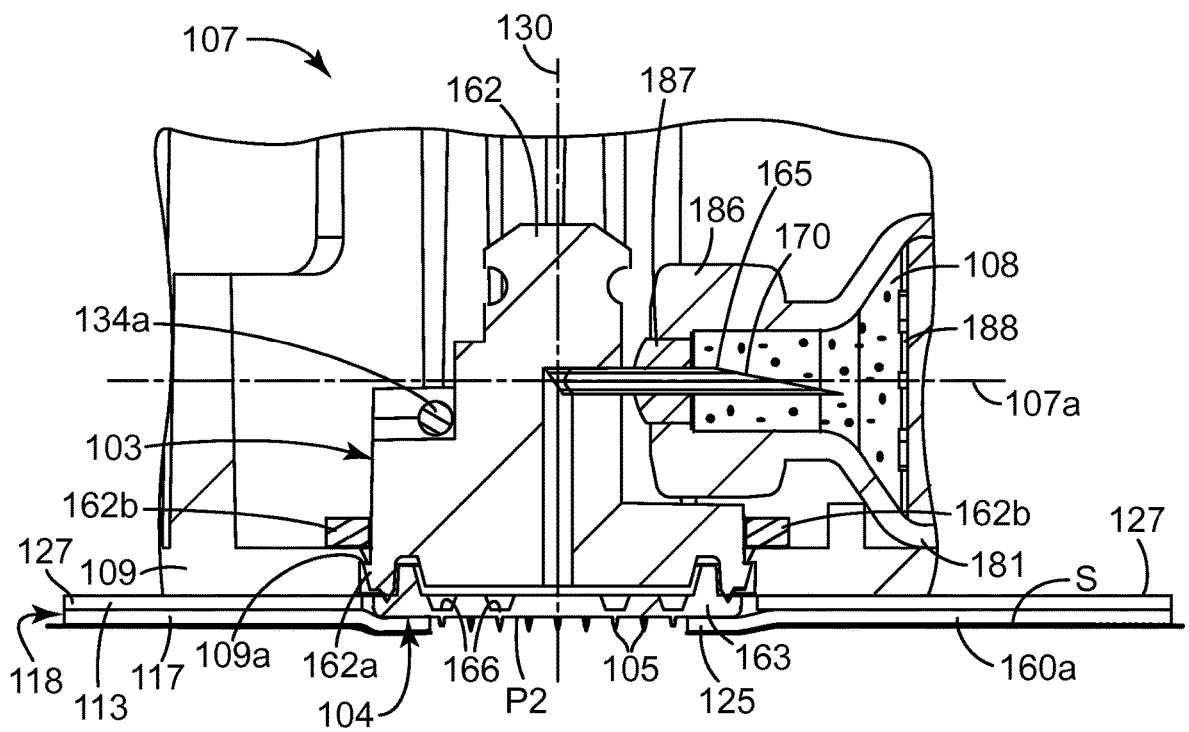
FIG. 12 is an enlarged schematic view of a portion of the microneedle injection apparatus of FIGS. 1-11, illustrating fluid communication of a drug cartridge with the microneedle applicator.
Figure 13A:
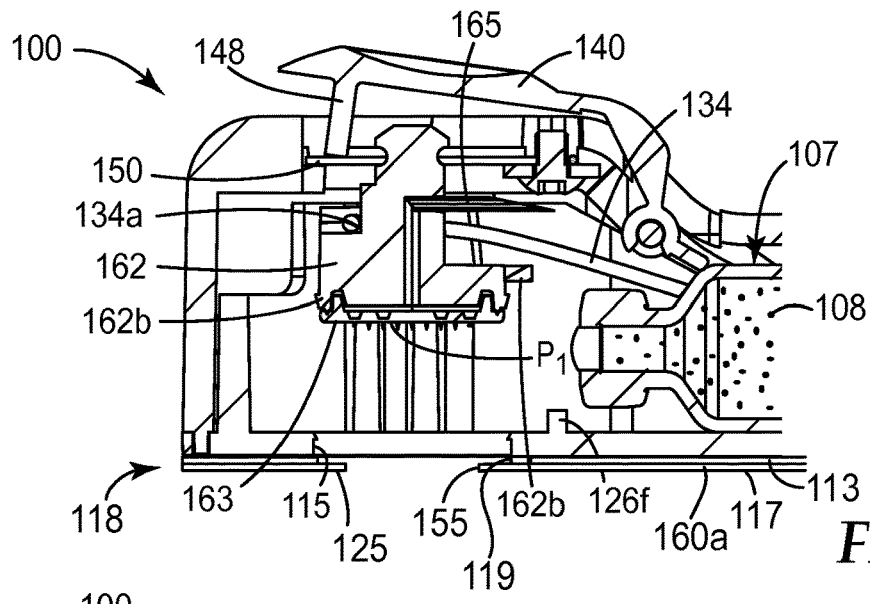
FIG. 13A is a partial view in cross-section of the microneedle injection apparatus of FIGS. 1-12, the apparatus shown in a primed condition.
Figure 13B:
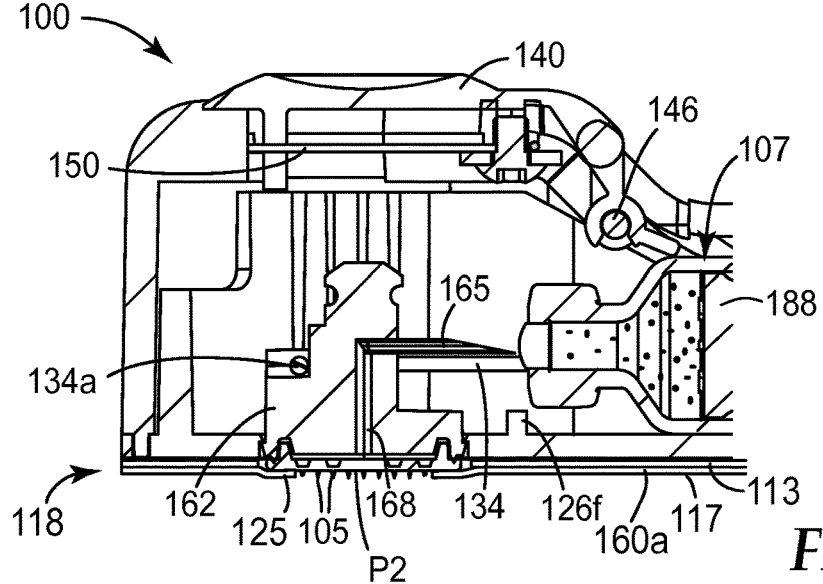
FIG. 13B is a partial view in cross-section of the microneedle injection apparatus of FIGS. 1-13A, illustrating hollow microneedles penetrating skin.
Figure 13C:
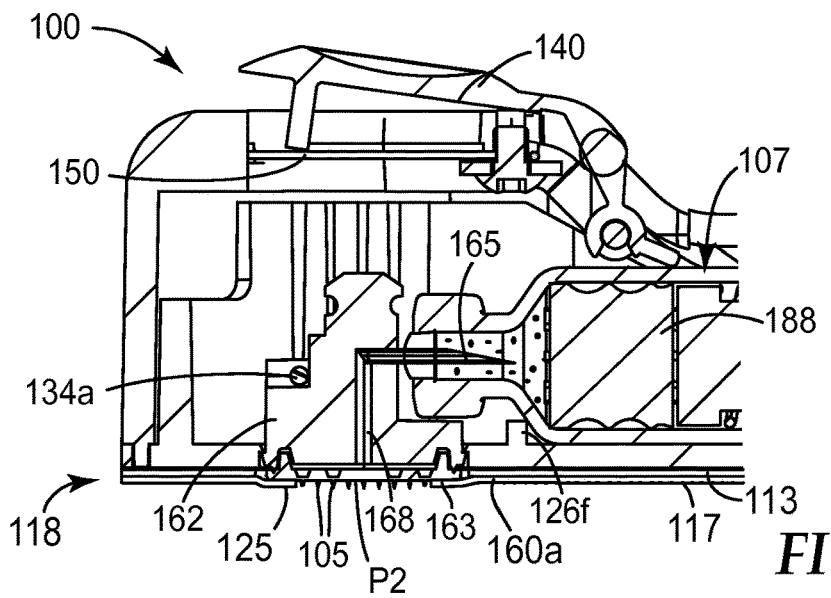
FIG. 13C is a partial view in cross-section of the of the microneedle injection apparatus of FIGS. 1-13B, showing transfer of the fluid from a drug cartridge to the microneedle applicator.

As illustrated in FIG. 12, for example, the microneedle array 104 may be fixedly connected as, for example, by ultrasonically welding it to the manifold carrier 162. For example, the present description envisions holding the microneedle applicator plate 163 to the manifold carrier 162 by a variety of techniques including, but not limited to, snap-fits, adhesives, such as a UV curable adhesive, medical adhesives, and other similar approaches. While fixed connections are described, releasable connections may be provided, such as in situations involving reusing the microneedle injection apparatus, whereby used microneedles may be replaced. In an illustrated embodiment, the releasable couplings include pressure-sensitive adhesives and the like.

The present description envisions positively the holding manifold carrier 162 in a penetrating position (i.e., the second position $P_2$) for reasons that will be explained. Towards this end, the manifold carrier 162 has a peripheral rim portion 162a extending radially by an amount that creates a latching or interference fit, when the applicator 103 is in its second position $P_2$, with corresponding retaining lower housing portions 109a (FIG. 12) of the lower housing portion 109. Also, the manifold carrier 162 may have an annular lateral projection 162b that is adapted to engage the lower housing portion 109 for even more robustly the stopping microneedle carrier 162. This interference fit and/or the lateral projection 162b can be sufficient to stop the manifold carrier 162 in the second position $P_2$ (useful, e.g., for penetrating a patient's skin). As such, in some embodiments, this may minimize the recoil effect of the first stored energy device 134 upon release, which recoil may, if unattenuated, cause hollow microneedles 105 to dislodge from a patient's skin following impact. As described above, the adhesive assembly 118 can also aid in minimizing recoil and in retaining the microneedles 105 in the skin to a desired depth.

The microneedle applicator plate 163 may be made from polymeric materials including, but not limited to, polycarbonate, liquid crystal polymer (LCP), acrylics including polymethyl methacrylate, ABS (Acrylontitrile butadiene styrene), polypropylene, nylon, polyetheretherketone, and combinations thereof.

The material making up the microneedles 105 themselves can be (or include) silicon, glass, or a metal such as stainless steel, titanium, or nickel titanium alloy. In some embodiments, the microneedle material can be (or include) a polymeric material, preferably a medical grade polymeric material. Exemplary types of medical grade polymeric materials include polycarbonate, liquid crystal polymer (LCP), polyether ether ketone (PEEK), cyclic olefin copolymer (COC), polybutylene terephthalate (PBT). Preferred types of medical grade polymeric materials include polycarbonate and LCP.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

Figure 6:
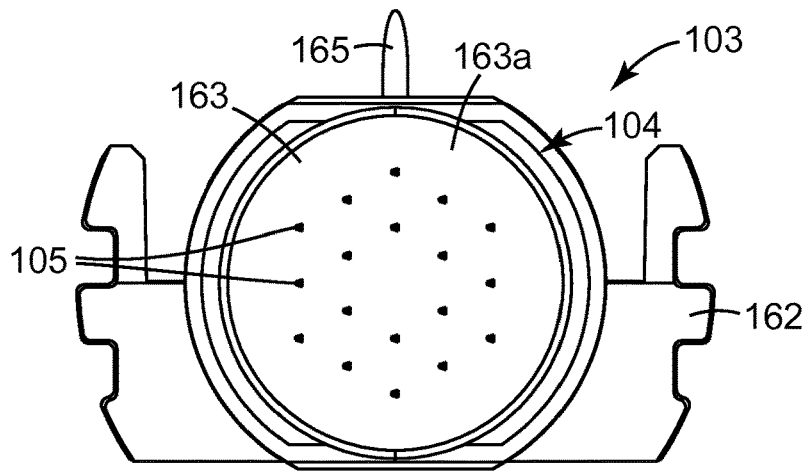
FIG. 6 is a bottom plan view of the microneedle applicator of FIG. 5, illustrating an array of hollow microneedles.
Figure 7:
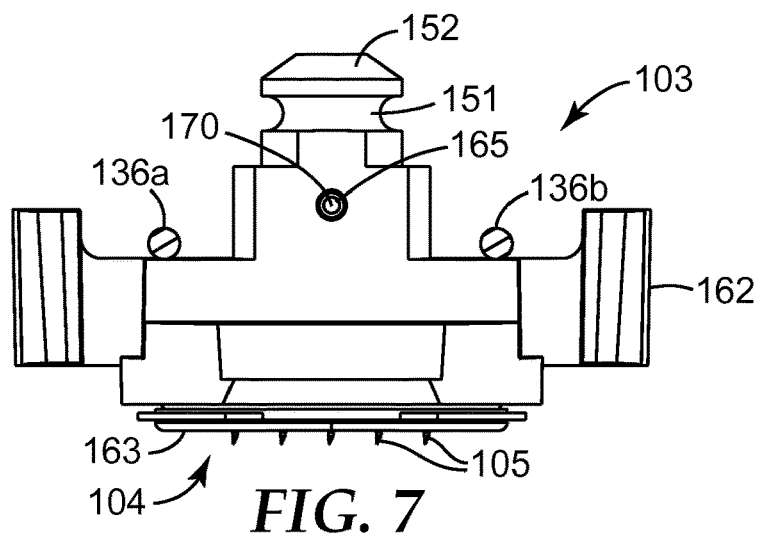
FIG. 7 is an end elevational view of the microneedle applicator of FIGS. 5 and 6, illustrating an array of hollow microneedles.

As shown in FIGS. 3 and 6, the microneedle applicator plate 163 has a generally annular peripheral rim portion 163a free of the hollow microneedles 105 and sized to enable a priming tool to engage it, thereby enabling priming of microneedle injection apparatus 100. As shown in FIG. 3, the extension 125 of the adhesive assembly 118 can overlap the peripheral rim portion 163a (also referred to as the "sidewalk" above). The present illustrated exemplary embodiment illustrates peripheral rim portion 163a. It will be appreciated that other similar microneedle-free portions thereof may be provided for cooperation with a priming tool and the adhesive assembly 118 (e.g., the extension 125). Alternatively or additionally, the present description allows for pulling of the applicator 103 to its first position $P_1$. In this regard, a tool (not shown), such as pliers or the like, may be used to pull upwardly on, for example, the upper retaining member 152. Other approaches are contemplated for pushing or pulling the applicator 103 for priming purposes.

Reference is now made to, for example, FIGS. 2, 9, 10, and 12. Fluid storage and delivery system 106 may include the reservoir 107 that is cooperable with a second stored energy device 180. As will be described, the second stored energy device 180 is operable to provide forces for opening an openable end of a reservoir to establish a fluid pathway to the applicator 103 and then causing the flow of the fluid 108 from the reservoir 107 to the hollow microneedles 105 on the microneedle applicator 103. In this embodiment, while a single spring is illustrated, a wide variety of other approaches can be contemplated.

While the reservoir 107 is described in the exemplary embodiment as a drug cartridge, the present description envisions the use of a wide variety of reservoirs having a variety of sizes and constructions that function similarly. In this exemplary embodiment, the reservoir 107 may include an elongated and relatively thin-walled tubular glass cylinder 181. The glass cylinder 181 may be annealed, transparent, have hydrolytic resistance to the fluids being used, and be strong enough to resist cracking or otherwise bursting when pressurized in the manner as described herein. In an illustrated exemplary embodiment, glass drug cartridges typically have their lubricity enhanced, such as by using a silicone (e.g., baked and/or liquid). Other materials for the reservoir drug cartridge may include, but are not limited to, polymers of various types including a polyolefin to avoid reaction to contained fluids. Polymers normally possess friction coefficients that permit piston travel.

The glass cylinder 181 has an end 182 that is openable and a plunger end 184. Openable end 182 is typically closed and sealed by an end cap 185. The end cap 185 may be secured to a neck portion of the glass cylinder 181 at its end 182. The end cap 185 may include a metallic cap 186, such as an aluminum cap, that is crimped to the end 182 in a known manner. The end cap 185 may hold a septum 187 (see FIG. 12) that sealingly closes an otherwise open end 182.

The septum 187 may be made of many different materials including those typically used with reservoirs (e.g., drug cartridges). The septum 187 may be made of a pierceable and resealable elastomeric seal or septum that is securely mounted, with or without being crimped, across the end 182. Typically, elastomers may be crimped onto an end of a glass cylinder, with material, such as aluminum. Other similar septum materials and modes of securing it to the end of the glass cylinder 181 may be used. For example, a molded-in septum of a material may be used, such as West Pharmaceutical Services, Inc, so-called CZ series, a cap, such as a standard syringe luer cap, or a molded end thin enough to be pierced. A variety of materials may be used that are subject to piercing with sufficient piercing force and which may maintain a seal once pierced. As noted, septum 187 is pierced during use and seals the piercing needle with enough force to prevent leakage during transfer of fluid from reservoir 107. Some known septum materials are contemplated that allow the septum to reseal following withdrawal of a needle after use. The present description envisions unsealing or opening the otherwise closed septum 187 by a variety of approaches.

The reservoir 107 includes a piston 188 that is in sliding and sealing relationship with respect to interior walls of glass cylinder 181. This provides adequate sealing for a fluid storable in an interior variable volume chamber formed between the piston 188 and the end 182. The chamber may be sized to have a volume of fluid to accommodate an intended dosage(s). Such a reservoir 107 (e.g., a drug cartridge) may be of the type wherein pre-filled drugs are ready-to-be used, such as the fluids noted above. The glass cylinder 181 may be of the kind that satisfies standards, including international standards, such as the International Organization for Standards (ISO). In addition, the glass cylinder 181 can be relatively easily cleanable and sterilizable which are highly advantageous features should it be desirable to reuse. Other components of the reservoir 107 may also be made to satisfy standards, such as ISO standards.

Drug cartridges of the kind noted offer advantages in that they are ready-to-use, versatile from the standpoint that the medical community tends to use them relatively easily and economically in supplying fluids and dosages that are customizable to individual patients. Also, such drug cartridges may be reusable following cleaning and sterilization by techniques known in the industry. This kind of drug cartridge may be easily refilled by known approaches utilized in the field. As such, its use in the microneedle injection apparatus of the present description provides several significant advantages.

While not shown, the present description also envisions the use of valve mechanisms for opening an openable end of a drug cartridge or reservoir for allowing transferring of a fluid to the hollow microneedles. For example, a valve member retained in a reservoir similar to the drug cartridge may be opened from a fluid blocking or closed condition by having it cooperate with structure (not shown), for example a cannula, on the microneedle applicator assembly, as the two are brought into operative engagement. However, piercing a sealing septum, as noted above, is a simplified and cost effective approach for establishing fluid communication.

Referring back to the piston 188, it is adapted to travel along a length of the reservoir 107 until the fluid 108 is completely (or nearly completely) forced or expressed therefrom. Typically, the piston 188 may be made of materials that seal against the body of the reservoir 107, but that are also inert with respect to the fluid 108. For example, purified cyclo-butyl materials may be typically used for such pistons, but silicones are also contemplated. Other similar materials include, but are not limited to, polypropylene, methylpentene, cyclic olefin polymers, and cyclic olefin copolymers. In addition, the piston 188 may be made of diverse materials including laminated constructions. While the illustrated embodiment uses one kind of piston, others may be utilized.

Reference is made back to FIGS. 8-10, 12, and 13A-13C. As mentioned above the reservoir 107 has a longitudinal axis 107*a* that is, in one exemplary embodiment, adapted to be generally parallel to a patient's skin S as well as the base 114 of the housing 102. Of course, the reservoir 107 may be disposed at other angles relative to the skin and the housing assembly. Such angling may allow, for instance, for allowing gravity to assist in the evacuation of the reservoir 107. For further keeping a low profile of the microneedle injection apparatus 100, the longitudinal axis 107*a* is generally normal to the vertical axis 130. In some respects, this compact geometric arrangement is advantageous. The reservoir 107 can be a transparent glass drug cartridge, in one exemplary embodiment, for enabling visual observations relating to the progress of fluid dispensing. This is advantageous particularly in infusion situations that may take relatively long periods. Such a glass drug cartridge may be of a commercially available type, such as from Schott North America, Elmsford, N.J., USA, and West Pharmaceutical Services, Inc. of Lionsville, Pa., USA. Other kinds of reservoirs having similar properties are envisioned.

The reservoir 107, when made of glass, may also be advantageous in regard to enhancing the versatility of the microneedle injection apparatus 100. An advantage offered by the present description is that the reservoirs 107 have sizes and shapes many pharmacists in the field are typically familiar with in regard to filling them. Also, because the reservoir 107 may be separate from the microneedle injection apparatus 100, users may be able to use reservoirs particularly formulated for themselves and then easily install them in the microneedle injection apparatus 100. Moreover, by being able to use known drug cartridges, patients are able to use a wide variety of drugs and dosages dispensed in a manner particularly tailored to them and not be dependent on a manufacturer of the dispensers having fixed reservoirs. The present description is in sharp contrast to known microneedle apparatus and systems that have dedicated or fixed fluid reservoirs of preselected sizes. Further, the latter category may additionally require special efforts to fill, as well as sterilize and refill.

A glass drug cartridge reservoir 107 may have dimensions that range from about 2 cm to about 7 cm in terms of their lengths, and may have inner diameters that range from about 4 mm to about 12 mm. More typically, the lengths may range from 4 cm to 6 cm, and the inner diameters from about 6 mm to about 10 mm. The present description contemplates other dimensions depending on, for example, the size of the drug dispensing cartridges. While a transparent glass drug cartridge reservoir 107 may be utilized, other materials may also be used. These materials and construction should be compatible to the fluids contained, and be able to withstand the pressures generated during use.

Also, while drug cartridges may be transparent, they need not be, but could instead be provided with a window(s) for allowing observations of the piston forcing the fluid during the dispensing process. Also, the present description envisions that other kinds of generally tubular containers may be used as well that are consistent with the present description. This is significant in terms of overall versatility in treating patients.

The present description envisions a microneedle injection apparatus 100 that contemplates single-use for such drug cartridges, but also replacing them, much like cassettes. By separating the drug cartridge from the other portions of the microneedle injection apparatus, the two can be made independently and are more easily customized to accommodate a variety of factors including, but not limited to, a variety of drugs, patients, as well as infusion times.

In the illustrated embodiment, a spring release 190 (see FIGS. 9 and 10) is operated to release the second stored energy device 180. As will be explained, the stored fluid in the reservoir 107 will be released following establishment of a fluid passage by the cooperation of the piercing needle 165 with the septum 187. In one exemplary embodiment, as shown, the second stored energy device 180 can include an elongated coil spring. The second stored energy device 180 may be released by the spring release 190. The spring release 190 may include a latch 192 that is coupled at one end to the plunger 194 abutting the piston 188. The second stored energy device 180 is interposed between the plunger 194 and the rear wall portion 126d to be loaded in a manner that provides sufficient operating forces for displacing the reservoir 107 when the second stored energy device 180 is released by the spring release 190.

Figure 14:
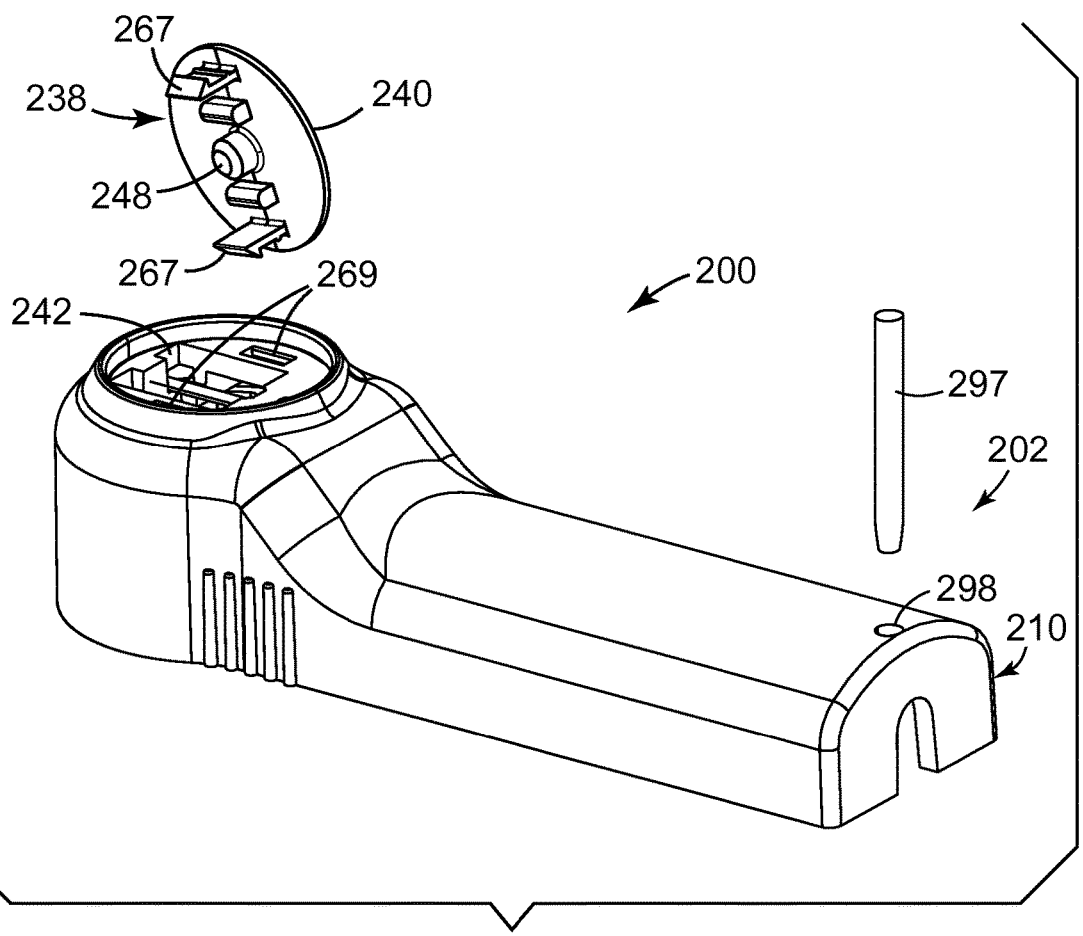
FIG. 14 is a partial exploded perspective view of microneedle injection apparatus according to another embodiment of the present disclosure, the microneedle injection apparatus including an alternative actuator (i.e., comprising a push-button) and an alternative spring release mechanism (i.e., employing a pin).
Figure 15:
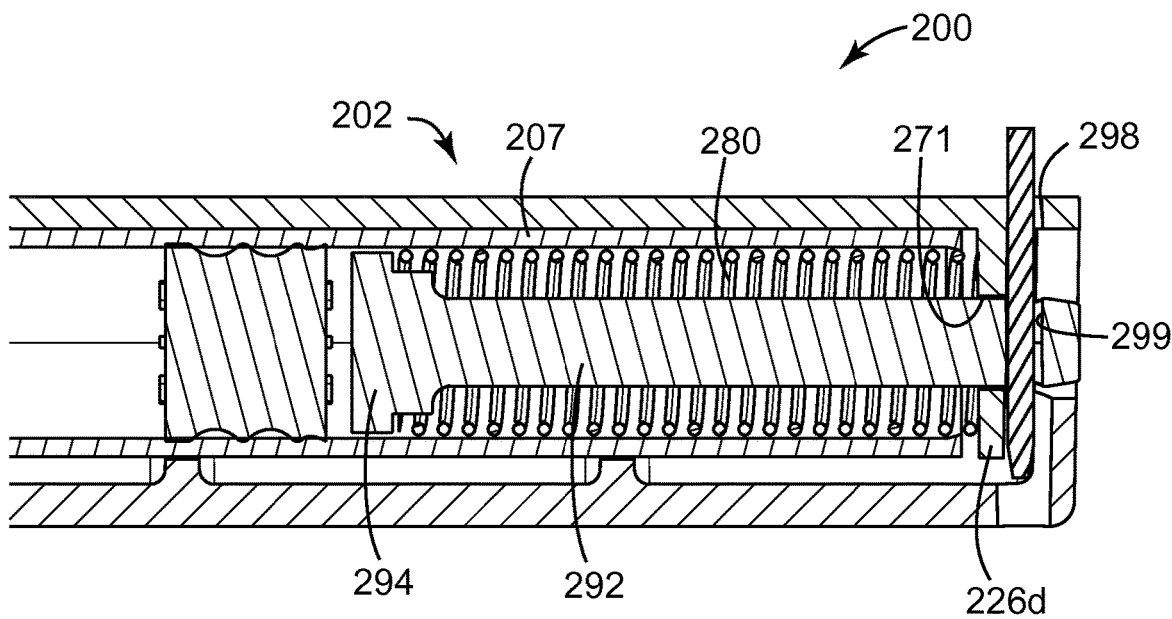
FIG. 15 is a partial side cross-sectional view of the microneedle injection of FIG. 14.

The latch 192 and the plunger 194 may be separate from each other but may be coupled. They may be made of similar or dissimilar materials, such as suitable plastics and metal. The latch 192 may be elongated as illustrated or may have a shorter length. A longer length facilitates removal of the second stored energy device 180 from the reservoir 107 as will be described. A projection 196 of the latch 192 is coupled to the rear wall portion 126d (FIG. 9), thereby retaining the second stored energy device 180 in a latched and loaded condition. While the projection 196 on the latch 192 is illustrated for cooperating with the retaining wall, the present description envisions other spring release mechanisms, similar to the kinds defined above. One example is illustrated in FIGS. 14-15 and described below.

To release the second stored energy device 180, a user merely lifts the latch 192 from engagement with the rear wall portion 126d. The second stored energy device 180 then displaces the reservoir 107 axially until it reaches stop 126f (FIG. 13A-13C) on the lower housing portion 109.

The piercing needle 165 pierces septum 187 after the applicator 103 has reached its second position $P_2$ (see FIGS. 10, 12, 13B and 13C). A fluid passage is established between the reservoir 107 and the microneedle applicator 103 for communicating fluid therebetween. As a result, the fluid 108 (FIG. 13A) is forced through the now opened septum 187 under the influence of the second stored energy device 180 pushing the piston 188. The fluid may enter the piercing needle 165 and the second stored energy device 180 is allowed to force the piston 188 forwardly to compress the chamber and force fluid therefrom into the applicator 103. From the piercing needle 165, the fluid flows into the fluid pathway 168 and the carrier reservoir 166 into the hollow microneedles 105. Because of the automatic operation provided by the second stored energy device 180 on the reservoir 107, the forces acting on the system can be controlled generally regardless of user-applied forces. This is advantageous over other systems that require manual pushing and/or sliding of a member in order to affect a release and dispensing of fluids. As noted, manual pushing or pulling forces may inadvertently cause issues. As such, this may cause the hollow microneedles to dislodge, thereby defeating the intended results of the apparatus.

To replace used drug cartridges, a user may pull on the latch 192 with a suitable hand tool (not shown) to recompress the second stored energy device 180. As such, a user can separate the piercing needle 165 and the septum 187. Consequently, the reservoir 107 and the latch 192 may be removed. It will be understood that a new drug cartridge may be replaced in the microneedle injection apparatus 100 for the one removed. Thus, in such embodiments, a user need only replace a cartridge instead of ordering a new device. In regard to adding a new drug cartridge, the second stored energy device 180 may be reused as well as the latch 192 and the plunger 194. Also, the microneedle array 104 should be replaced as well.

Consequently, the manufacturer or even the user may easily install a ready-to-use reservoir 107. This may be accomplished by inserting a drug cartridge and then inserting a second stored energy device in their illustrated positions. By allowing the reservoir 107 and the second stored energy device 180 to be installed separately, shelf life can be enhanced since there is not a requirement for the coil spring to be constantly loaded against the drug cartridge for long periods.

The first and second stored energy devices of the present description may be comprised of at least one stored energy device from a group consisting of: spring devices, gaseous propellants, chemicals, electrical devices, and combinations thereof.

While the embodiment described above describes dual actuation, other embodiments may be employed that affect dual automatic operation in response to a user merely activating a single actuation device. Examples of such single actuation embodiments are described in US Patent Publication No. 2012/0123387 (Gonzalez et al.), which is incorporated herein by reference.

It will be further understood that provisions are made for a method of treating a patient by infusing a fluid using an apparatus of the present disclosure.

While the above embodiments have been described as being accomplished in particular sequences, it will be appreciated that such sequences of the operations may change and still remain within the scope of the present description. Also, other procedures may be added.

Release Liner

Release liners suitable for use with the adhesive assemblies and microneedle injection apparatuses of the present disclosure can include, but are not limited to, kraft papers, polyethylene, polypropylene, polyester, or combinations thereof. Such liners can be coated with release agents, such as fluorochemicals, silicones, or other suitable low surface energy materials. Other adhesives and release liner combinations known to those of ordinary skill in the art can also be employed in the medical dressings of the present disclosure. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films, commercially available from H. P. Smith Co., and fluoropolymer coated polyester films, commercially available from 3M Company (St. Paul) under the brand "SCOTCHPAK™" release liners.

Adhesives

In some embodiments, the securing adhesive 137 and first adhesive layer 141 can have an adhesion that is higher than the skin-contact adhesive 136. In some embodiments, the securing adhesive 137, 141 and the skin-contact adhesive 136 may be of the same or similar classes of adhesive, but have different adhesions. For example, changes in adhesive composition, adhesive thickness, or adhesive surface area can change the adhesion. For example, the securing adhesive 137, 141 and/or the skin-contact adhesive 136 may be an acrylate, silicone, urethane, hydrogel, hydrocolloid, natural rubber, or synthetic rubber.

"Adhesion" refers to the force required to separate an adhesive from an underlying substrate. Adhesion can be measured in a number of ways. For example, adhesion can be defined by peel force or shear force. In some embodiments, adhesion can be defined by peel adhesion using ASTM D3330/D3330M-04(2010). In some embodiments, adhesion can be defined by shear adhesion using ASTM D3654M-06(2011). Adhesion is highly dependent on the specific substrate being adhered to, as well as the time the pressure-sensitive adhesive (PSA) is allowed to dwell on the substrate.

For example, typical peel adhesion values exhibited by pressure-sensitive adhesives in medical dressings maybe in the range of 20 to 300 g/cm as measured from stainless steel. In some embodiments, at least 10% higher peel adhesion, as measured by ASTM D3330/D3330M-04(2010), of the securing adhesive 137, 141 over the skin-contact adhesive 136 may realize the benefit of both securing to the housing 102 (and securing the first layer 113 of the adhesive assembly 118 to the second layer 117), while providing gentle adhesion to the skin.

In some embodiments, the securing adhesive 137, 141 can be an acrylate adhesive and the skin-contact adhesive 136 can be a silicone adhesive. The term "acrylate" or "acrylate-based" or "acrylate-containing" refers to monomeric acrylic or methacrylic esters of alcohols. Acrylate and methacrylate monomers are referred to collectively herein as "acrylate" monomers. Materials that are described as "acrylate-based" or "acrylate-containing" contain at least some acrylate monomers and may contain additional co-monomers.

Acrylate adhesives are well suited for securing the adhesive assembly 118 to the housing 102 or to skin. The adhesion can be manipulated to have high adhesion or low adhesion.

Suitable acrylate adhesives that can be applied to skin such as the acrylate copolymers are described in U.S. Pat. No. RE 24,906, the disclosure of which is hereby incorporated by reference. In particular, a 97:3 iso-octyl acrylate:acrylamide copolymer. Another acrylate adhesive is an 70:15:15 isooctyl acrylate:ethyleneoxide acrylate:acrylic acid terpolymer, as described in U.S. Pat. No. 4,737,410 (Example 31), the disclosure of which is hereby incorporated by reference. Other useful acrylate adhesives are described in U.S. Pat. Nos. 3,389,827, 4,112,213, 4,310,509, and 4,323,557, the disclosures of which are incorporated herein by reference.

The term "silicone" or "silicone-based" or "silicone-containing" refers to polymers that contain units with dialkyl or diaryl siloxane (—SiR$_2$O—) repeating units. The silicone-based polymers may be segmented copolymers or polysiloxanes polymers. The terms silicone and siloxane are used interchangeably.

Generally, silicone adhesives are able to effectively adhere the microneedle injection apparatus 100 to skin and upon removal from the skin produce little or no skin damage. Typically, the silicone adhesives do not adhere well to polymer-based substrates, like tubing or hardgoods. The gentle removal of silicone adhesives from skin make silicone adhesives well suited as the skin-contact adhesive 136.

An example of a suitable silicone adhesive is disclosed in PCT Publications WO2010/056541 and WO2010/056543, the disclosures of which are incorporated herein by reference. A radiation-cured silicone adhesive is particularly well suited for this application because the extent of crosslinking, and therefore adhesion of the silicone adhesive can be better controlled. Other examples of silicone gel adhesives systems include products marketed with the trade names: Dow Corning MG 7-9850, Wacker SILPURAN® 2110 and 2130, Bluestar SILBIONE® RT Gel 4317 and 4320, Nusil MED-6345 and 6350.

For skin-contact adhesives, it is desirable that the adhesive is able to transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as perforating the adhesive or pattern coating the adhesive, as described in U.S. Pat. No. 4,595,001 and U.S. Pat. App. Pub. 2008-0233348, the disclosures of which are incorporated herein by reference. Each of the securing or skin-contact adhesive can optionally be applied in a discontinuous manner.

Additional exemplary embodiments of microneedle injection apparatuses and adhesive assemblies of the present disclosure will now be described with respect to FIGS. 14-21. FIGS. 14-21 illustrate various microneedle injection apparatuses or adhesive assemblies of the present disclosure, wherein like numerals represent like elements. The microneedle injection apparatuses and adhesive assemblies of FIGS. 14-21 share many of the same elements, features, and functions as the microneedle injection apparatus 100 and the adhesive assembly 118 described above with respect to FIGS. 1-13C. Reference is made to the description above accompanying FIGS. 1-13C for a more complete description of the features and elements (and alternatives to such features and elements) of the embodiments illustrated in FIGS. 14-21. Any of the features described above with respect to FIGS. 1-13C can be applied to the embodiments of FIGS. 14-21, and vice versa.

FIG. 14-15 illustrate a microneedle injection apparatus 200 according to another embodiment of the present disclosure. A microneedle injection apparatus having the features of the microneedle injection apparatus 200 was used in the examples. The microneedle injection apparatus 200 includes a housing 202 (and particularly, only an upper housing portion 210 of the housing 202 is shown in FIG. 14 for simplicity); an actuator opening 242 in the housing 202; an actuator 238 comprising a finger engageable portion 240 adapted to cover the actuator opening 242; and a spring release 290. The microneedle injection apparatus 200 includes many similarities with the microneedle injection apparatus 100 of FIGS. 1-13C, except that the microneedle injection apparatus 200 includes an alternative configuration for the finger engageable portion 240 and the spring release 290.

Specifically, as shown in FIG. 14, the finger engageable portion 240 does not pivot with respect to the housing 202. Rather, the finger engageable portion 240 is in the form of a push-button. As such, the finger engageable portion 240 includes one or more prongs 267 dimensioned to be received in slots 269 formed in the housing 202 within the actuator opening 242, and a plunger 248 which acts to press downwardly on an upper retaining member of a microneedle applicator (e.g., the upper retaining member 152 of the applicator 103 of FIGS. 9, 10, 12 and 13A-13C). The plunger 248 is positioned such that when the finger engageable portion 240 is depressed into the housing 202, the plunger 248 presses downwardly on the upper retaining member of microneedle applicator, which forces legs (e.g., 150a and 150b) of a resilient engaging device (e.g., resilient engaging device 150) apart, causing the legs to release a peripheral groove (e.g., the peripheral groove 151) of the upper retaining member, thereby releasing the microneedle applicator (e.g., from its first position $P_1$), allowing the applicator to be carried downwardly (e.g., to a second position $P_2$) by a stored energy device (e.g., the first stored energy device 134), as described above with respect to FIGS. 1-13C. The prongs 267 can be flanged and can be configured to snap into the slots 269 in two positions—(i) a first position in which the prongs 267 are positioned in the slots 269 such that the finger engageable portion 240 is engaged with the housing 202 and does not easily fall out, but in which the plunger 248 is not pressing on the upper retaining member of the applicator; and (ii) a second position in which the prongs 267 are fully seated in the slots 269 and the plunger 248 presses on the upper retaining member.

As detailed in FIG. 15, the microneedle injection apparatus 200 also includes an alternative spring release 290. Specifically, the microneedle injection apparatus 200 includes a latch 292, a plunger 294, and a second stored energy device 280. Rather than the projection 196 of the microneedle injection apparatus 100, the spring release 290 includes a pin 297 which is dimensioned to be received in an aperture or bore 298 in the housing 202 as well as an aperture 299 in the latch 292. The end of the latch 292 comprising the aperture 299 can be passed through an opening 271 in rear wall portion 226d to a position in which the apertures 298 and 299 are aligned. The pin 297 can then be positioned in the aperture 298 of the housing 202 and the aperture 299 in the latch 292, thereby retaining the end of the latch 292 passed the rear wall portion 226d and the second stored energy device 280 in a latched and loaded condition. To release the second stored energy device 280, a user merely lifts the pin 297 from engagement with the latch 292 (and optionally pulls the pin 297 entirely out of the housing 202). The second stored energy device 280 then displaces a reservoir 207 axially until it reaches a stop (not shown in FIG. 15 but see 126f of FIGS. 13A-13C). Fluid communication from the reservoir 207 to an applicator then proceeds as described above with respect to the microneedle injection apparatus 100. Replacing used drug cartridges can also follow the method described above.

FIGS. 16-21 illustrate adhesive assemblies according to other embodiments of the present disclosure. In each of FIGS. 16-21, only an adhesive layer (i.e., a "second layer") is illustrated for simplicity and clarity. As described above with respect to the second layer 113, each of the adhesive layers of FIGS. 16-21 can also be formed of one or more adhesive layers and will be referred to as an "adhesive layer" for simplicity. It should be understood that the adhesive assembly of the present disclosure can include any one of the adhesive layers of FIGS. 16-21 alone, or in combination with the first layer 113 described above. The different adhesive layer configurations can be employed, at least partially depending on the microneedle applicator and microneedle array arrangement with which the adhesive assembly will be used.

Figure 16:
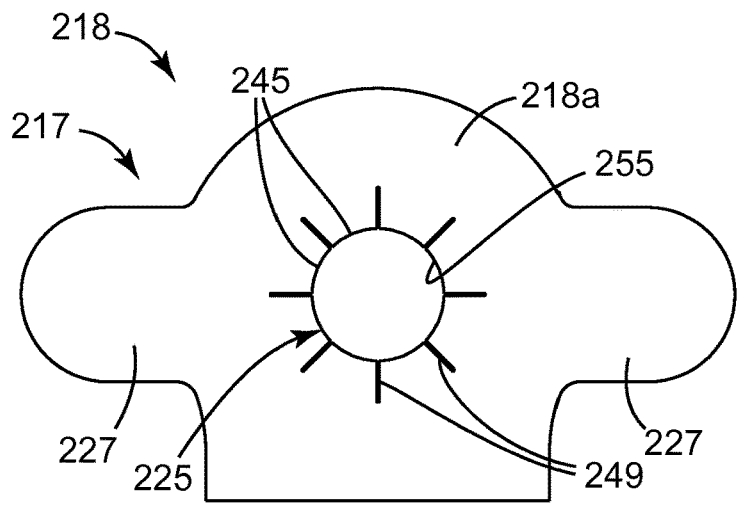
FIG. 16 is a top plan view of an adhesive layer according to another embodiment of the present disclosure.

FIG. 16 illustrates an adhesive assembly 218 according to another embodiment of the present disclosure. The adhesive assembly 218 includes an adhesive layer (or "second layer") 217 comprising an annular portion 218a flanked on two sides by tabs 227; and an extension 225 comprising a plurality of portions or sections 245 separated by vents 249 and defining an opening 255 that is sized to accommodate a microneedle array. While the vents 149 of the adhesive assembly 118 have a width or thickness and are in the form of slots, the vents 249 of the adhesive assembly 218 are in the form of slits, such that no (or very little) material is removed from the extension 225 in forming the vents 249.

Figure 17:
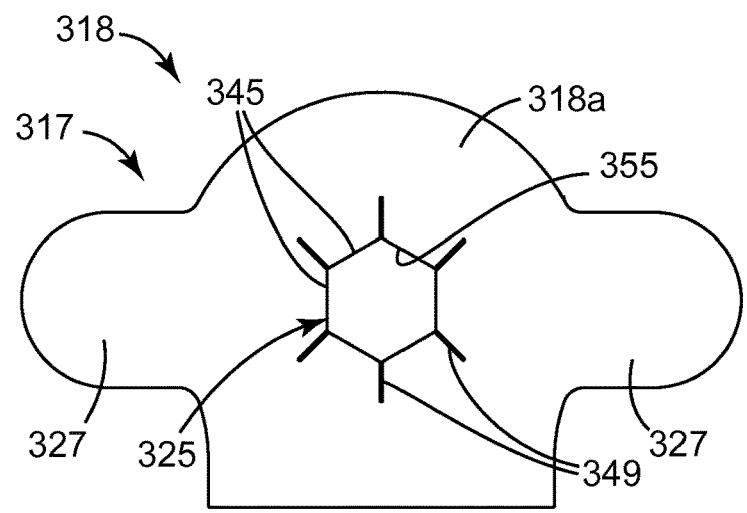
FIG. 17 is a top plan view of an adhesive layer according to another embodiment of the present disclosure.

FIG. 17 illustrates an adhesive assembly 318 according to another embodiment of the present disclosure. The adhesive assembly 318 includes an adhesive layer (or "second layer") 317 comprising an annular portion 318a flanked on two sides by tabs 327; and an extension 325 comprising a plurality of portions or sections 345 separated by vents 349 in the form of slits and defining an opening 355 that is sized to accommodate a microneedle array. The adhesive assembly 318 is substantially the same as the adhesive assembly 218 of FIG. 16, except that the opening 255 is circular in shape, while the opening 355 of the adhesive assembly 318 is hexagonal in shape. It should be understood that the shape, size and configuration of any extension of an adhesive assembly of the present disclosure can be configured to accommodate a desired microneedle array and that a variety of shapes and configurations can be employed without departing from the spirit and scope of the present disclosure.

Figure 18:
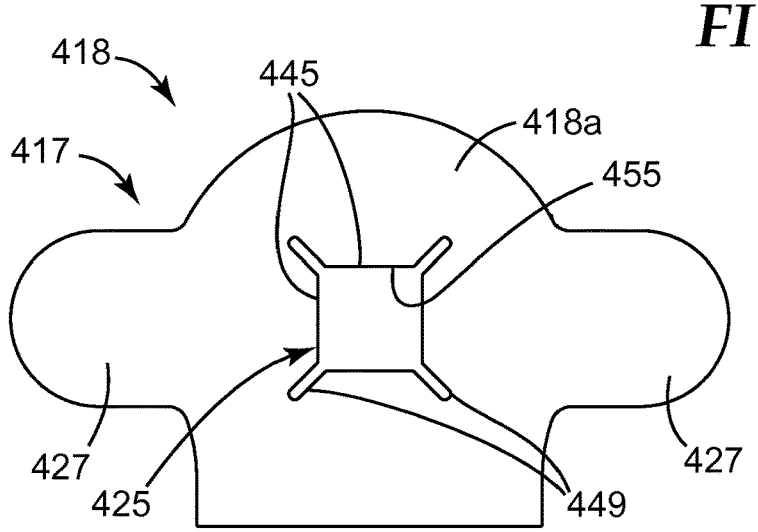
FIG. 18 is a top plan view of an adhesive layer according to another embodiment of the present disclosure.

FIG. 18 illustrates an adhesive assembly 418 according to another embodiment of the present disclosure. The adhesive assembly 418 includes an adhesive layer (or "second layer") 417 comprising an annular portion 418a flanked on two sides by tabs 427; and an extension 425 comprising a plurality of portions or sections 445 separated by vents 449 and defining an opening 455 that is sized to accommodate a microneedle array. The vents 449 are formed similar to the vents 149 of FIGS. 2-3C. By way of example only, the opening 455 is square in shape, and the vents 449 each extend radially outwardly at each of the corners of the square opening 455. However, it should be understood that other vent configurations and numbers can be employed.

Figure 19:
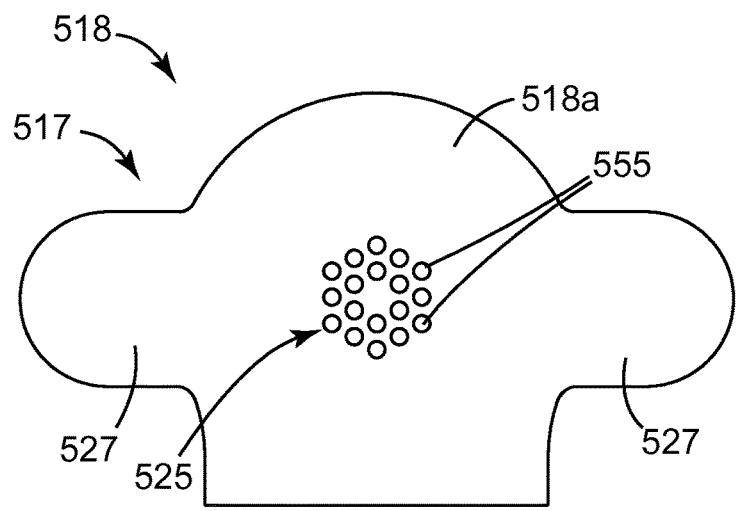
FIG. 19 is a top plan view of an adhesive layer according to another embodiment of the present disclosure.

FIG. 19 illustrates an adhesive assembly 518 according to another embodiment of the present disclosure. The adhesive assembly 518 includes an adhesive layer (or "second layer") 517 comprising an annular portion 518a flanked on two sides by tabs 527; and a continuous extension 525 comprising a plurality of openings 555 that are each dimensioned to receive a microneedle (or cluster of microneedles) of a microneedle array. That is, the extension 525 is an example of an extension that extends across an area defined by an opening in a base of a microneedle injection apparatus and around and adjacent the microneedles. The overall arrangement of the openings 555 is configured to accommodate a specific microneedle array configuration, and by way of example only, the plurality of openings 555 are arranged in an overall hexagonal shape. However, it should be understood that other configurations and arrangements are possible and can be tailored to specific array configurations. The adhesive assembly 518 does not include any vents and represents an example of an unvented adhesive assembly.

Figure 20:
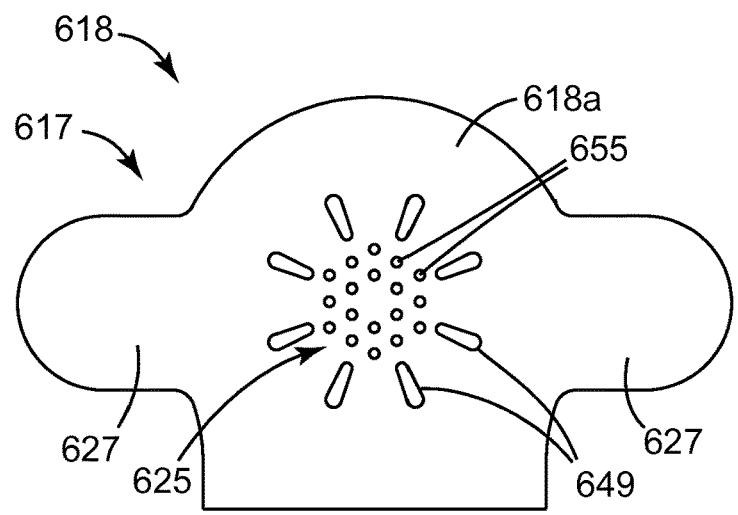
FIG. 20 is a top plan view of an adhesive layer according to another embodiment of the present disclosure.

FIG. 20 illustrates an adhesive assembly 618 according to another embodiment of the present disclosure. The adhesive assembly 618 includes an adhesive layer (or "second layer") 617 comprising an annular portion 618a flanked on two sides by tabs 627; and a continuous extension 625 comprising a plurality of openings 655 that are each dimensioned to receive a microneedle (or cluster of microneedles) of a microneedle array. That is, the extension 625 is another example of an extension that extends across an area defined by an opening in a base of a microneedle injection apparatus and around and adjacent the microneedles. The plurality of openings 655 are also shown in a hexagonal arrangement by way of example only. The adhesive assembly 618 further includes vents 649 which, by way of example only, are arranged to extend radially outwardly beyond the arrangement of openings 655, e.g., in a sunburst pattern.

Figure 21:
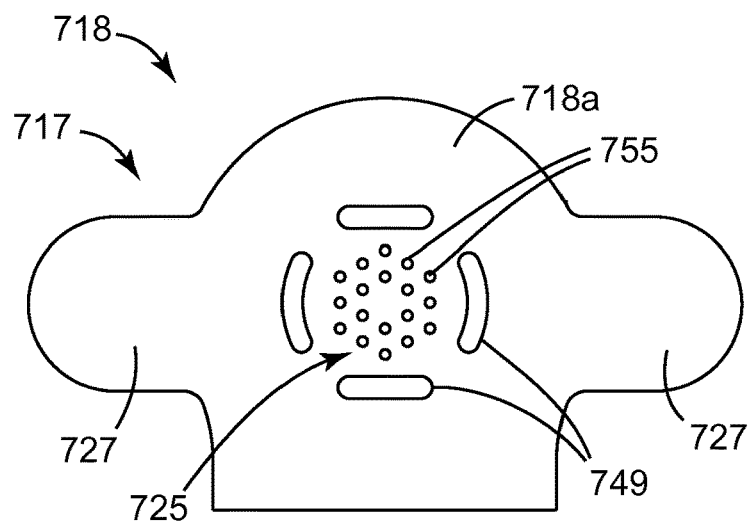
FIG. 21 is a top plan view of an adhesive layer according to another embodiment of the present disclosure.

FIG. 21 illustrates an adhesive assembly 718 according to another embodiment of the present disclosure. The adhesive assembly 718 includes an adhesive layer (or "second layer") 717 comprising an annular portion 718a flanked on two sides by tabs 727; and a continuous extension 725 comprising a plurality of openings 755 that are each dimensioned to receive a microneedle (or cluster of microneedles) of a microneedle array. That is, the extension 725 is another example of an extension that extends across an area defined by an opening in a base of a microneedle injection apparatus and around and adjacent the microneedles. The plurality of openings 755 are also shown in a hexagonal arrangement by way of example only. The adhesive assembly 718 further includes vents 749 which, by way of example only, are arranged to extend around the plurality of openings 755 in form of two arcuate and opposing slots and two flat and opposing slots.

The adhesive assemblies 118, 218, 318, 418, 518, 618 and 718 are illustrated and described by way of example only, and it should be understood that other adhesive assembly configurations and extension configurations and arrangements are possible, including various combinations of the various adhesive assemblies 118, 218, 318, 418, 518, 618 and 718.

Each embodiment shown in the figures is illustrated as a separate embodiment for clarity in illustrating a variety of features of the microneedle injection apparatuses and adhesive assemblies of the present disclosure. However, it should be understood that any combination of elements and features of any of the embodiments illustrated in the figures and described herein can be employed in the microneedle injection apparatuses and adhesive assemblies of the present disclosure.

The following embodiments are intended to be illustrative of the present disclosure and not limiting.

EMBODIMENTS

Embodiment 1 is a microneedle injection apparatus comprising:
 a housing having a base and an opening formed in the base, the opening defining an area;
 an applicator comprising a microneedle array, the microneedle array comprising a first major surface and a plurality of microneedles that protrude from the first major surface, the applicator movable between
  a first position in which the microneedle array is recessed within the housing such that the microneedle array does not extend beyond the base of the housing, and
  a second position in which at least a portion of the microneedle array extends through the opening in the base and beyond the base of the housing; and
 an adhesive assembly adhered to the base of the housing, the adhesive assembly including an extension that extends at least partially into the area defined by the opening, such that when the applicator is in the second position, at least a portion of the first major surface of the microneedle array is in contact with the extension of the adhesive assembly.

Embodiment 2 is the apparatus of embodiment 1, wherein the extension extends only partially into the area defined by the opening.

Embodiment 3 is the apparatus of embodiment 1 or 2, wherein the extension is in the form of an annulus and defines an opening therein, the opening sized to contain the plurality of microneedles.

Embodiment 4 is the apparatus of any of embodiments 1-3, wherein the adhesive assembly includes a first side configured to adhere to the base of the housing, and a second side configured to adhere to a skin surface.

Embodiment 5 is the apparatus of any of embodiments 1-4, wherein the adhesive assembly includes a first side positioned toward the base of the housing and a second side opposite the first side.

Embodiment 6 is the apparatus of embodiment 5, wherein the extension of the adhesive assembly includes adhesive on at least the second side.

Embodiment 7 is the apparatus of embodiment 5 or 6, wherein the extension of the adhesive assembly includes adhesive on the first side and the second side, such that the first side of the extension is configured to adhere to the first major surface of the microneedle array and the second side of the extension is configured to adhere to the skin, when the applicator is in the second position.

Embodiment 8 is the apparatus of any of embodiments 1-7, wherein the adhesive assembly comprises:
 a first layer configured to be coupled to the base of the housing and including an opening that aligns with the opening in the base of the housing, and
 a second layer comprising the extension and including a skin-contact adhesive.

Embodiment 9 is the apparatus of embodiment 8, wherein the first layer includes a shock-absorbing layer.

Embodiment 10 is the apparatus of embodiment 8 or 9, wherein the first layer includes a first side configured to be coupled to the base of the housing and a second side opposite the first side, and wherein the second layer includes at least one layer of adhesive.

Embodiment 11 is the apparatus of embodiment 10, wherein the first side of the first layer includes an adhesive configured to adhere the first side of the first layer to the base of the housing.

Embodiment 12 is the apparatus of embodiment 10 or 11, wherein the second layer includes a first adhesive layer configured to adhere to the second side of the first layer and the first major surface of the microneedle array, and a second adhesive layer comprising a skin-contact adhesive.

Embodiment 13 is the apparatus of embodiment 12, wherein the extension is formed by the first adhesive layer and the second adhesive layer of the second layer.

Embodiment 14 is the apparatus of any of embodiments 1-13, wherein the extension is continuous about a periphery of the opening.

Embodiment 15 is the apparatus of any of embodiments 1-13, wherein the extension is discontinuous about a periphery of the opening to define a plurality of vents between discontinuous portions of the extension.

Embodiment 16 is the apparatus of any of embodiments 1-13 and 15, wherein the extension is discontinuous and includes a plurality of portions, and wherein each portion of the extension is separated by a vent.

Embodiment 17 is the apparatus of embodiment 15 or 16, wherein each vent extends outwardly from the microneedle array.

Embodiment 18 is the apparatus of any of embodiments 1-13 and 15-17, wherein the extension includes a plurality of portions that each extend from a location adjacent a periphery of the opening at least partially into the area defined by the opening.

Embodiment 19 is the apparatus of any of embodiments 1-18, wherein the applicator is configured to be moved from the first position to the second position at a velocity of at least 5 m/s.

Embodiment 20 is the apparatus of any of embodiments 1-19, wherein the first major surface of the microneedle array contacts the adhesive assembly when the applicator is moved to the second position.

The following working examples are intended to be illustrative of the present disclosure and not limiting.

EXAMPLES

Example 1—Apparatus

Fully assembled apparatuses (200) of the embodiment described in FIGS. 14 and 15 were prepared. The housing components of the apparatus were molded from LEXAN 3412R-131 (SABIC, Pittsfield, Mass.). The external housing (202) was about 98 mm in length with a width of about 32 mm at the rounded end section (see, e.g., 126c of FIG. 2) of the apparatus (section housing the applicator and microneedle array). The width of the external housing in the lateral wall section (see, e.g., 126a and 126b of FIG. 2) of the apparatus (section housing the cartridge reservoir and second stored energy device) was about 27 mm. The height of the external housing in the rounded section was 27 mm and the height at the opposite end containing the lateral wall section was about 17 mm. The opening in the lower housing (see, e.g., 115 of FIGS. 2 and 3) was in the shape of a barrel or "race-track". The dimensions of the opening were about 16 mm by 13 mm. The base member (114) of the molded lower housing was about 1.6 mm thick. Prior to attachment of the adhesive assembly (160a), the section of the first major surface (116) that was to be joined to the adhesive assembly was milled to remove 0.76 mm of material.

The hollow microneedle array (104) was molded from Vectra MT1300 liquid crystal polymer (LCP) (Ticona Engineering Polymers, Florence, Ky.) in the shape of a circle approximately 1.25 cm in diameter. The base portion of the array (e.g., the microneedle applicator plate 163) was about 0.8 mm thick. The array featured 18 hollow microneedles (105) arranged in pattern of two concentric hexagons centered on the array. The perimeter of the outer hexagon was composed of twelve evenly spaced microneedles and the perimeter of the inner hexagon was composed of six evenly spaced microneedles. The microneedles extended from the first major surface of the base portion of the array. Each microneedle was in the shape of a conventional hypodermic needle with a pointed beveled tip. The spacing between neighboring microneedles was about 2 mm (as measured from tip to tip). Each microneedle had a height of about 900 microns with an aspect ratio of about 3:1.

The resilient engaging device (150) was a U-shaped leaf-like spring prepared from 302 stainless steel. The diameter of the wire was 1.19 mm. The two leg portions (150a, 150b) of the spring were about 20.8 mm in length with a gap distance of about 3.8 mm.

The first stored energy device (134) was a U-shaped leaf-like spring prepared from heat treated 17-7PH stainless steel. The diameter of the wire was 1.59 mm. The two leg portions (134b, 134c) of the spring were about 79 mm in length with a gap distance of about 12 mm.

The applicator (103) was molded from Vectra MT 1300 thermoplastic liquid crystal polymer (LCP) (Ticona Engineering Polymers, Florence, Ky.). The piercing needle (165) was integrally formed with the applicator and had the shape of a single bevel hypodermic needle. The length of the piercing needle was about 6.2 mm with a bore size of 0.66 mm.

The hollow microneedle array was attached to the applicator portion of the apparatus by ultrasonically welding the second major surface of the base portion of the array to the applicator. The travel distance of the microneedle array from its recessed position in the primed state to its final resting position after actuation was about 10 mm. After actuation, the final resting position of the base of the microneedle array extended beyond the first major surface (116) of the base (114) of the lower housing by a distance of about 2.3 mm.

The drug cartridge reservoir component (107) included a 3.0 mL siliconized glass cylinder (181) (Gerresheimer AG, Dusseldorf, Germany) that was 62.3 mm in length and 11.6 mm in diameter. An aluminum end cap (186) was crimped to the neck portion of the glass cylinder. The end cap was fitted with a bromobutyl rubber septum (187) (catalog no. FM457, Datwyler Pharma Packaging, Inc., Pennsauken, N.J.). The piston element (188) fitted into the opening at the plunger end (184) of the glass cylinder was also constructed from bromobutyl rubber (catalog no. 4023/50, West Pharmaceutical Services, Lionville, Pa.). The drug cartridge reservoir component was filled with a 1 mL solution of 0.005% methylene blue in five percent aqueous dextrose solution.

The second stored energy device (280) was a coiled spring prepared from heat treated 17-7PH stainless steel. The spring specifications required a load force of 10.9 N for the spring compressed to 52.6 mm and a load force of 12.7 N for the spring compressed to 39.1 mm.

The spring release element (290) was molded from LEXAN 3412R-131 and consisted of a plunger portion (194) and a latch portion (292). The plunger and latch were formed as a single integrated unit. The head of the plunger was about 9.1 mm in diameter and 4.5 mm thick. The overall length of the spring release element (plunger and latch) was about 36.6 mm. A small aperture (299) was positioned in the latch about 2 mm from the free end of the latch (i.e. end without the plunger head). The compressed coiled spring (280) was coupled to the spring release element (290) by positioning the compressed coiled spring between the plunger of the release element and the small aperture in the latch. A small tapered pin (297) was inserted in the hole in the arm to hold the compressed spring in place.

The pin (297) inserted in the latch was aligned with and inserted through the complementary aperture (298) in the housing. When inserted through both the aperture in the latch and the aperture in the housing, the pin served to attach the spring release element to the housing. Removal of the pin released the coiled spring (280) from the stored (pre-activated) condition.

The upper and lower housings of the fully assembled apparatus were secured to each other by wrapping two strips of 12.7 mm wide polyimide film tape (available from the 3M Company, St. Paul, Minn., catalog number 5413) around the lateral wall portions of the housing sections. The two tape strips were separated by about 4 cm.

The adhesive assembly (160a) was a laminate composed of four layers (FIGS. 3A and 3B). The first layer was a 0.10 mm thick sheet of 3M 1510 double sided tape (available from the 3M Company). The second layer was a 0.32 mm thick sheet of SONTARA® 8005, a spun-laced, polyester non-woven fabric (DuPont Corporation, Wilmington, Del.). The third layer was a 0.10 mm sheet of 3M 1510 double sided tape. The fourth layer was a 0.07 mm sheet of 3M 1524 transfer adhesive. The adhesive assembly was positioned to cover the first major surface (116) of base member of the lower housing at the rounded end section of the device. The adhesive assembly laminate was laser cut so that the size and shape of the adhesive assembly was matched to that of the device. As depicted in FIG. 3.3, the dimensions L1 and L2 of the adhesive assembly were about 32 mm and 55 mm (tab to tab distance), respectively. The first and second layers of the adhesive assembly each contained cut-out regions that were aligned to each other and exactly matched the opening in the device housing. The third and fourth layers each contained a cut-out opening (155) 8.9 mm in diameter with eight evenly spaced vents (149) arranged to extend radially outwardly from the edge of the opening. Each vent (149) had a width of about 0.9 mm and a length of about 2.7 mm. The openings in layers three and four were aligned with each other and in addition the center of the openings in layers three and four were aligned with the center of openings in layers one and two. The two tabs (127) on the adhesive assembly were used to aid in removing the device from the skin. Each tab was integral with the adhesive assembly and extended about 11 mm from the edge of the device. A release liner was attached to both surfaces of each tab. The device and adhesive assembly were oriented so that the first layer of the adhesive assembly was adhered to the first major surface (116) of the lower housing of the device. The adhesive assembly was aligned with the device so that the opening (119) in the first layer of the adhesive assembly was coincident with the opening (115) in the device. A release liner was used during storage of the device to protect the exposed adhesive of the fourth layer of the adhesive assembly.

Example 2—Apparatus

The same apparatus as described in Example 1 was constructed with the exception that the wire diameter of the first stored energy device (134) was 1.50 mm instead of 1.59 mm.

Example 3—Apparatus

The same apparatus as described in Example 1 was constructed with the exception that the wire diameter of the first stored energy device (134) was 1.40 mm instead of 1.59 mm.

Example 4—In Vivo Study

The study was conducted using Yorkshire cross domestic pigs (Midwest Research Swine, Gibbon, Minn.) in vivo. The ham area was selected as the application site for microneedle insertion. The application site was first trimmed with an electric clipper and then shaved using a razor and shaving cream. The shaved area was scrubbed using soapy water and a BUF-PUF exfoliation sponge (3M Company, St. Paul, Minn.) and then rinsed with deionized water. The animal was placed in a lateral recumbent position on a heated table (38° C.). The animal was anesthetized with isofluorene gas and maintained under anesthesia throughout the experiment. The application site was then wiped with a 70% isopropanol in water solution.

The release liner was removed from the non-tab portion of the adhesive assembly described in Example 1 and the apparatus (200) of Example 1 was subsequently adhered to the skin of the pig. The push-button (240) was depressed to release the applicator element and to insert the microneedle array into the skin of the pig. The insertion speed of the array (m/s) was determined using a Keyence LK-H087 laser displacement sensor (Keyence America, Elmwood Park, N.J.) operating at 100 kHz. Removal of the tapered pin (297) from the housing released the coiled spring (280) which initiated the injection of the methylene blue solution into the pig. After completion of the injection, the apparatus was maintained on the skin for one additional minute. The apparatus was removed from the skin and the skin surface was examined to determine if there was any methylene blue solution on the surface of the skin. The presence of methylene blue solution on the skin was an indication that not all of the methylene blue was injected into the animal. The injection site was wiped with a pre-tared absorbent wipe and the wipe was then weighed to determine the amount of methylene blue that was not successfully delivered.

A total of six replicates were conducted. The average insertion speed of the microneedle array was about 9.0 m/s. The average injection time was about 160 seconds. All six of the apparatuses successfully delivered the methylene blue solution without any "leakage" (i.e. no methylene blue solution was observed on the skin surface).

Example 5—In Vivo Study

The procedure as described in Example 4 was used with the exception that the apparatus of Example 2 was used instead of the apparatus of Example 1.

A total of eight replicates were conducted. The average insertion speed of the microneedle array was about 8.3 m/s. The average injection time was about 214 seconds. The impact force of the array on the skin was calculated to be about 30 N. Six of the eight apparatuses successfully delivered the methylene blue solution without any "leakage" (i.e. no methylene blue solution was observed on the skin surface). For one apparatus, 14 mg of the methylene blue solution was recovered from the skin surface and for another apparatus 1 mg of the methylene blue solution was recovered from the skin surface.

Example 6—In Vivo Study

The procedure as described in Example 4 was used with the exception that the apparatus of Example 3 was used instead of the apparatus of Example 1.

A total of six replicates were conducted. The average insertion speed of the microneedle array was about 7.1 m/s. The average injection time was about 190 seconds. All six of the apparatuses successfully delivered the methylene blue solution without any "leakage" (i.e. no methylene blue solution was observed on the skin surface).

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:
1. A microneedle injection apparatus comprising:
a housing having a base and an opening in the base, the opening in the base defining an area;
an applicator comprising a microneedle array, the microneedle array comprising a first major surface and a plurality of microneedles that protrude from the first major surface, the applicator movable between
- a first position in which the microneedle array is recessed within the housing such that the microneedle array does not extend beyond the base of the housing, and
- a second position in which at least a portion of the microneedle array extends through the opening in the base and beyond the base of the housing; and an adhesive assembly adhered to the base, the adhesive assembly including a plurality of adhesive extensions that extend at least partially into the area defined by the opening in the base, such that when the applicator is in the second position, at least a portion of a first major surface of the microneedle array is in contact with at least a portion of each of the plurality of adhesive extensions of the adhesive assembly, wherein the adhesive assembly includes a first side positioned toward the base and a second side opposite the first side, and further wherein each of the plurality of adhesive extensions of the adhesive assembly include adhesive on a first side and a second side wherein the second side of each of the plurality of adhesive extensions is the second side of the adhesive assembly and further wherein the first side of each of the plurality of adhesive extensions is configured to adhere to the first major surface of the microneedle array and the second side of each of the plurality of adhesive extensions is configured to adhere to skin, when the applicator is in the second position, and further wherein the plurality of adhesive extensions are separated by vents and arranged to define an opening in the adhesive assembly.

2. The apparatus of claim 1, wherein the plurality of adhesive extensions extend only partially into the area defined by the opening in the base.

3. The apparatus of claim 1, the opening in the adhesive assembly is in a form of an annulus, the annulus being sized to contain the plurality of microneedles.

4. The apparatus of claim 1, wherein the first side of the adhesive assembly is configured to adhere to the base, and the second side of the adhesive assembly is configured to adhere to a surface of the skin.

5. The apparatus of claim 1, wherein the adhesive assembly comprises:
- a first layer configured to be coupled to the base and including, and
- a second layer comprising the plurality of adhesive extensions.

6. The apparatus of claim 5, wherein the first layer includes a shock-absorbing layer.

7. The apparatus of claim 5, wherein the first layer includes the first side of the adhesive assembly that is configured to be coupled to the base and a second side opposite the first side, and wherein the second layer includes at least one layer of adhesive.

8. The apparatus of claim 7, wherein the first side of the first layer of the adhesive assembly includes an adhesive of the adhesive assembly that is configured to adhere the first side of the first layer to the base.

9. The apparatus of claim 7, wherein the second layer of adhesive assembly includes a first adhesive layer and a second adhesive layer, wherein the first adhesive layer is configured to adhere to the second side of the first layer and the first major surface of the microneedle array, and wherein the second adhesive layer comprises a skin-contact adhesive.

10. The apparatus of claim 9, wherein the plurality of adhesive extensions are formed by the first adhesive layer and the second adhesive layer of the second layer.

11. The apparatus of claim 1, wherein the plurality of adhesive extensions are discontinuous about a periphery of the opening in the base to define vents.

12. The apparatus of claim 1, wherein the plurality of adhesive extensions extend from a location adjacent a periphery of the opening in the base to at least partially into the opening in the base.

13. The apparatus of claim 1, wherein the first major surface of the microneedle array contacts the adhesive assembly when the applicator is moved to the second position.

14. The apparatus of claim 1, wherein the applicator is configured to be moved from the first position to the second position at a velocity of about 2 m/s to about 20 m/s.

15. The apparatus of claim 1, wherein the plurality of adhesive extensions are positioned such that at least a portion of the microneedle array strikes and adheres to at least a portion of the plurality of adhesive extensions while the microneedle array is traveling from the first position to the second position.

16. The apparatus of claim 1, wherein the plurality of extensions are discontinuous and the plurality of vents extend outwardly from the opening of the adhesive assembly.

* * * * *